US00RE39342E

(19) United States
(12) Reissued Patent
Starks et al.

(10) Patent Number: US RE39,342 E
(45) Date of Reissued Patent: Oct. 17, 2006

(54) METHOD FOR PRODUCING A SYNTHESIZED STEREOSCOPIC IMAGE

(75) Inventors: Michael Starks, Springfield, OR (US); Alan Shulman, Mill Valley, CA (US)

(73) Assignee: For3D, Inc., Santa Rosa, CA (US)

(21) Appl. No.: 10/226,807

(22) Filed: Aug. 22, 2002

Related U.S. Patent Documents

Reissue of:
(64) Patent No.: 6,108,005
Issued: Aug. 22, 2000
Appl. No.: 08/905,574
Filed: Aug. 4, 1997

U.S. Applications:
(60) Provisional application No. 60/024,900, filed on Aug. 30, 1996.

(51) Int. Cl.
*G06T 15/10* (2006.01)
*G06T 15/70* (2006.01)

(52) U.S. Cl. ..... 345/419; 345/473; 345/629; 348/42; 382/118

(58) Field of Classification Search ..... 345/419, 345/629, 473, 647, 8, 649, 9, 121, 653, 660, 345/654, 665, 672, 679, 680; 348/42, 56, 348/51, 47; 382/118
See application file for complete search history.

(56) References Cited

U.S. PATENT DOCUMENTS

| | | | | | |
|---|---|---|---|---|---|
| 3,621,127 | A | * | 11/1971 | Hope | 348/56 |
| 4,393,400 | A | * | 7/1983 | Ikushima et al. | 348/56 |
| 4,414,565 | A | * | 11/1983 | Shanks | 348/44 |
| 4,523,226 | A | * | 6/1985 | Lipton et al. | 348/49 |
| 4,562,463 | A | * | 12/1985 | Lipton | 348/56 |
| 4,582,117 | A | * | 4/1986 | Kushnick | 164/463 |
| 4,625,290 | A | * | 11/1986 | White | 345/419 |
| 4,683,217 | A | * | 7/1987 | Lok et al. | 502/214 |

(Continued)

FOREIGN PATENT DOCUMENTS

| | | | |
|---|---|---|---|
| EP | 0 219 435 A2 | * | 4/1987 |
| EP | 0 219 435 B1 | * | 11/1990 |
| EP | 0 716 330 A2 | * | 6/1996 |
| EP | 0 716 330 A3 | * | 10/1996 |
| WO | WO83/02706 | * | 4/1983 |
| WO | WO96/13944 | * | 5/1996 |
| WO | WO/9618925 | * | 6/1996 |
| WO | WO97/24000 | * | 3/1997 |

*Primary Examiner*—Sumati Lefkowitz
*Assistant Examiner*—Chante Harrison
(74) *Attorney, Agent, or Firm*—Finnegan, Henderson, Farabow, Garrett & Dunner LLP

(57) ABSTRACT

Methods, devices and systems are provided which produce a synthesized stereoscopic image of a source image by forming at least two images from a source image where at least one image has been modified relative to the source image such that the images have a different spacial appearance than each other. A wide variety of modifications may be made to the source object in order to form modified stereo images. These modifications may involve modifying one or more images relative to the source image. For example, at least one image may be magnified, reduced, or rotated in the X, Y and/or Z plane relative to the source image. Alternatively or in addition, the position of one or more elements of one of the images may also be changed relative to the source image. Alternatively or in addition, at least one of the images may be transformed relative to the source image using a function which alters the position of elements of the image along the X or Y axis relative to the source image. In one variation, the function is a distorting algorithm, for example an elliptical or aspheric distorting algorithm which is not dependent on the depth information of the source image.

61 Claims, 16 Drawing Sheets

U.S. PATENT DOCUMENTS 4,739,418 A * 4/1988 Iwahara et al. ..... 348/43
4,740,836 A * 4/1988 Craig ..... 348/49
4,862,292 A * 8/1989 Enari et al. ..... 360/8
4,877,307 A * 10/1989 Kalmanash ..... 359/465
4,925,294 A * 5/1990 Geshwind et al. ..... 352/57
4,979,033 A * 12/1990 Stephens ..... 348/56
4,994,989 A * 2/1991 Usami et al. ..... 345/420
5,155,750 A * 10/1992 Klynn et al. ..... 378/42
5,175,806 A * 12/1992 Muskovitz et al. ..... 345/582
5,193,000 A * 3/1993 Lipton et al. ..... 348/43
5,212,562 A * 5/1993 Ogura ..... 386/88
5,239,372 A * 8/1993 Lipton ..... 348/58
5,293,227 A * 3/1994 Prince ..... 348/53
5,294,997 A * 3/1994 Ogura et al. ..... 386/95
5,410,644 A * 4/1995 Thier et al. ..... 345/582
5,416,510 A * 5/1995 Lipton et al. ..... 348/43
5,434,613 A * 7/1995 Dasso ..... 348/42
5,467,446 A * 11/1995 Mikkelsen et al. ..... 345/443
5,490,240 A * 2/1996 Foran et al. ..... 345/587
5,493,418 A * 2/1996 Takahashi et al. ..... 358/451
5,510,832 A * 4/1996 Garcia ..... 348/56
5,541,642 A * 7/1996 Ashbey ..... 348/59
5,553,203 A * 9/1996 Faris ..... 358/1.16
5,561,746 A * 10/1996 Murata et al. ..... 345/419
5,564,810 A * 10/1996 Larson ..... 353/8
5,594,843 A * 1/1997 O'Neill ..... 345/427
5,606,348 A * 2/1997 Chiu ..... 345/213
5,606,363 A * 2/1997 Songer ..... 348/49
5,612,709 A * 3/1997 Sudo et al. ..... 345/8
5,615,322 A * 3/1997 Murata et al. ..... 345/427
5,621,867 A * 4/1997 Murata et al. ..... 345/582
5,627,582 A * 5/1997 Muramoto et al. ..... 348/43
5,659,625 A * 8/1997 Marquardt ..... 382/118
5,850,352 A * 12/1998 Moezzi et al. ..... 345/419
5,867,588 A * 2/1999 Marquardt ..... 382/118

* cited by examiner

FIG. 7A
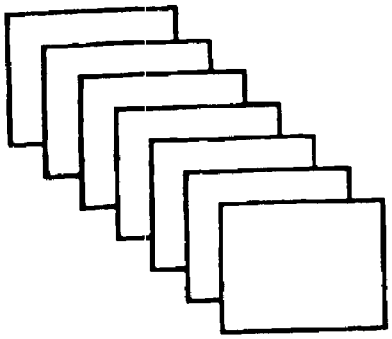
FIG. 7B
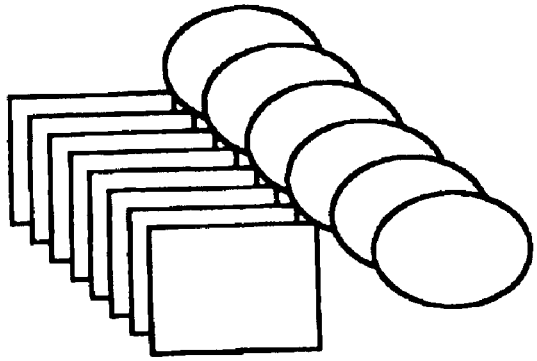
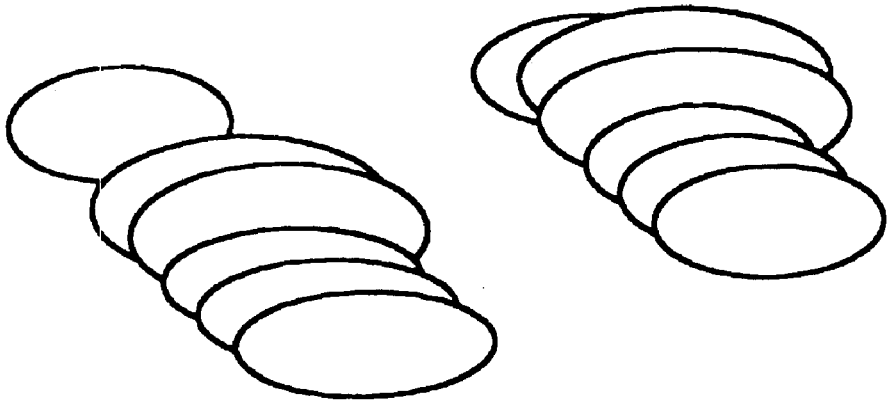
FIG. 7C

METHOD FOR PRODUCING A SYNTHESIZED STEREOSCOPIC IMAGE

Matter enclosed in heavy brackets [ ] appears in the original patent but forms no part of this reissue specification; matter printed in italics indicates the additions made by reissue.

[RELATIONSHIP TO COPENDING APPLICATION] *RELATED APPLICATIONS*

This application [is a continuation-in-part of "METHOD AND DEVICE FOR STEREOSYNTHESIS,"] *claims the benefit of priority of* U.S. Provisional Application Ser. No.: 60/024,900; filed: Aug. 30, 1996 which is incorporated herein by reference.

FIELD OF THE INVENTION

The present invention relates to methods, devices and display systems for converting source images to synthesized stereoscopic images and more specifically for forming two or more images from a source image where at least one image of the two or more images has been modified relative to the source image such that synthesized stereoscopic images are formed.

BACKGROUND OF THE INVENTION

Stereoscopic imagery for television and computer monitors is performed by presenting a different image to each eye of the observer. Images for each eye may be created and presented electronically, electrooptically and/or purely optically such that the human observer perceives a three dimensional image. Using these methods, it is possible to create complex three dimensional presentations which may be used in a wide variety of applications.

Most systems for producing stereoscopic imagery have depended on the use of true stereo pairs of images created by complex and costly optical or computer systems. Although there have been attempts to convert two dimensional images to three dimensional images using field delay with image shifting (e.g. U.S. Pat. No. 5,510,832), such conversions have not produced three dimensional imagery having sufficient quality. For example, it is not possible to create a quality three dimensional image of a still image using prior art methods since field delay may be required. Other transformations of such pairs of images from one encoding method to another has been also been difficult and costly because they generally require depth information and computation. Furthermore, it has been necessary to generate stereo pairs of images using two separate cameras or a single camera with special lenses. Such arrangements are costly and difficult to use.

A need therefore exists for a method and device for providing stereoscopic images which can be done rapidly and inexpensively. The device and method should also be able to form the stereoscopic image without substantially degrading the image or color.

SUMMARY OF THE INVENTION

The present invention relates to methods, logic, data signals, recorded data, devices and systems for use in providing a synthesized stereoscopic image from a source image by forming two or more modified stereo images from the source image where at least one of the modified stereo images has been modified relative to the source image such that at least two of the modified stereo images have a different spacial appearance than each other. The stereoscopic image formed may be used in a holographic display.

As used herein, "different spacial appearance" refers to a difference in the size and/or orientation of two images and/or a difference in the spacial relationship between elements of one image and the corresponding elements of the other image. The different spacial appearance can be perceived when the two images are displayed and compared. However, the images with a different spacial appearance can be expressed as data encoding the images which, when displayed, have a different spacial appearance. The images can also be expressed as data encoding a source image in combination with one or more algorithms for modifying the source image and producing two images which have a different spacial appearance.

As also used herein, "modified stereo images" refers to the two or more images derived from the source image where at least one image of the two or more images has been modified relative to the source image such that at least two of the two or more images have a different spacial appearance. These modifications to the images do not required knowledge of the relative depts of particular elements of the image. Modified stereo images can be in the form of two or more images being displayed as well as data encoding the two or more images which when displayed would have a different spacial appearance. Modified stereo images can be in the form of data encoding a source image in combination with one or more algorithms for modifying the source image and producing two or more images which have a different spacial appearance.

A wide variety of modifications may be made to the source object in order to form the modified stereo images. These modifications may involve modifying one or more of the images forming the modified stereo images relative to the source image. For example, at least one image of the modified stereo images may be magnified, reduced, or rotated in the X, Y and/or Z plane relative to the source image. Alternatively or in addition, the position of one or more elements of one of the modified stereo images may also be changed relative to the source image. Alternatively or in addition, at least one image of the modified stereo images may be transformed relative to the source image using a function which alters the position of elements of the image along the X or Y axis relative to the source image. In one variation, the function is a distorting algorithm, for example an elliptical or aspheric distorting algorithm.

As used herein, the source image may be any two or three dimensional image, holographic image or set of two or three dimensional images. Examples of source images include, but are not limited to motion picture film, photographs, computer images, video and tomographic data sets, such as those derived from MRI or CT data. The source images may be recorded, for example on VHS video tape, betacam SP or D1 tape, nonlinear edit system, time base corrector, computer floppy disc, computer hard drive, RAM, CDROM, laserdisc and DVD. The source image may also be provided via a live broadcast, video signals, or generated by a software program. The source image can also be an analog or digital set of data corresponding to one or more two or three dimensional images.

In one embodiment of the invention, a method is provided for producing a synthesized stereoscopic image by displaying modified stereo images having a different spacial appearance, and viewing the modified stereo images through stereo viewing glasses which transmit the spatially different images to left and right eyes of the viewer to form a synthesized stereoscopic image of the source image, such as a VR headset. In one variation of this embodiment, an image display is used to transmit the modified stereo images to the stereo viewing glasses. In a further variation, image signals encoding the modified stereo images are transmitted to the image display by a device which converts recorded data encoding the modified stereo images into image signals which are received by the image display. In yet another variation, image signals encoding the modified stereo images are transmitted to the image display by an image processor which converts a signal encoding the source image into signals encoding the modified stereo images. According to this variation, conversion of the signal encoding the source image into the signals encoding the modified stereo images is performed in real time. Conversion may alternatively be delayed. Conversion of the image signals may be an analog to analog, analog to digital, digital to digital, digital to analog, and/or in combination with optical to optical signal conversion.

Further, according to this variation, the signal encoding the source image may include a signal which provides instructions to the image processor regarding how to convert the signal encoding the source image into signals encoding the modified stereo images. These instructions may be simultaneously broadcast and may include, for example, image element by image element instructions or image frame by image frame instructions.

In another embodiment of the invention, a method is provided for producing a synthesized stereoscopic image using stereo viewing glasses which form modified stereo images. In this embodiment, the method includes displaying on an image display a source image, and viewing the source image through stereo viewing glasses, the stereo viewing glasses having left and right lenses, at least one of the lenses modifying the source image to produce at least two images having a different spacial appearance (modified stereo images) when viewed through the lenses. In one variation of this embodiment, modifying the source image to produce modified stereo images having a different spacial appearance is performed in real time. Alternatively, the modified stereo images are created and stored prior to being displayed. Modifying the source image can involve an analog to analog, analog to digital, digital to digital, digital to analog, and/or in combination with optical to optical signal conversion.

In another embodiment of the invention, a method is provided for converting a signal encoding a source image into recorded signals encoding two or more spatially different images which form a synthesized stereoscopic image of the source image when displayed in combination. In this embodiment, the method includes taking a signal encoding a source image, forming two or more image signals encoding the source image, modifying at least one of the two or more image signals such that at least two of the image signals encode images which have a different spacial appearance than each other, and recording signals encoding the modified stereo images. The signals encoding the modified stereo images may be recorded on a variety of different media including, for example magnetic media, VHS video tape, Betacam SP or D1 tape, nonlinear edit system, frame store, computer floppy disc, computer hard drive, RAM, CDROM, laserdisc, DVD, MPEG and other optical or digital device. Modifying at least one of the image signals can involve an analog to analog, analog to digital, digital to digital, digital to analog, and/or in combination with optical to optical signal conversion.

In another embodiment of the invention, a method is provided for synthesizing a stereoscopic image from a source image. According to this embodiment, the method includes taking a signal encoding a source image, forming two or more image signals encoding the source image, modifying at least one of the two or more image signals such that the two or more image signals encode at least a pair of images having a different spacial appearance, displaying on an image display the spatially different images encoded by the modified image signals, and viewing the image display through stereo viewing glasses which transmit the spatially different images to a left and right eye of the viewer to form a synthesized stereoscopic image of the source image. In one variation of this embodiment, modification of the image signals is performed in real time. Modifying at least one of the image signals can involve analog to analog, analog to digital, digital to digital, digital to analog, and/or in combination with optical to optical signal conversion.

In a variation of this embodiment, the two or more image signals encoding the source image includes a signal which provides instructions to an image processor regarding how to modify at least one of the two or more image signals. These instructions may include, for example, image element by image element instructions or image frame by image frame instructions. These instructions can be simultaneously broadcasted the image signals and can be combined with the image signals. For example, the instructions can be embedded into the signal, for example, in the vertical sync.

The present invention also relates to signals encoding two or more images which have a different spacial appearance which are derived from the same source image and which, when viewed in combination, form a synthesized stereoscopic image of the source image. These signals may be analog or digital signals. In one variation, the two or more images include two images which have a different spacial appearance than each other. In another variation, the two or more images include three images which have a different spacial appearance than each other. These signals may be transmitted signals or signals which are recorded on a recording media. In one particular embodiment, these signals are derived from a computer generated image which has been modified according to the present invention.

It is envisioned that larger bandwidth systems, such as HDTV, will be able to transmit and receive separate signals for each modified image used to form the synthesized stereoscopic image. Accordingly, the present invention is also intended to be used in combination with such higher bandwidth systems where two or more signals each encoding a modified stereo image is transmitted and/or received.

The present invention also relates to a recording of synthetic stereoscopic images according to the present invention. The recording includes a recording medium having recorded thereon two or more signals encoding at least two images having a different spacial appearance which, when viewed in combination, form a synthesized stereoscopic image. The recording may encode an analog or digital signal. Any recording media capable of storing dual image signals may be used, including, but not limited to VHS video tape, betacam SP or D1 tape, nonlinear edit system, computer floppy disc, computer hard drive, RAM, CDROM, laserdisc and DVD.

The present invention also relates to an image processor for converting a signal encoding a source image into a signal encoding a synthesized stereoscopic image. In one embodiment, the image processor includes a signal entry port for receiving a signal encoding a source image, logic for converting the source image into two or more image signals encoding the source image where at least one of the two or more image signals is modified such that the image signals encode two or more images having a different spacial appearance, and a signal exit port for transmitting the modified image signals.

The logic may act to convert the source image to the synthesized stereoscopic image in real or non-real time. The logic may be programmable or controllable by the user to form different modified stereo images. For example, the user can program the logic to make certain elements of an image or certain images appear closer or farther away. Alternatively or in addition, the logic may be designed to dynamically control how the image processor transforms the source image based on the source image. This dynamic control may be on a program by program, image by image or element by element basis. For example, the logic may include certain image element recognition protocols which cause certain elements to be selectively brought into the foreground or background when detected. In one embodiment, these protocols can be used to sense whether an image corresponds to a close-up or wide-angle perspective so that the image maybe modified accordingly. The logic may also include certain movement recognition protocols which detects movement of certain elements and causes the image to be modified in a particular manner in response to the detected movement. This adaptation is particularly useful in pan and scan applications where it is desirable to keep certain image elements, such as an actor, centered in the image.

In a variation of this embodiment, the image processor also receives one or more signals which accompany the signal encoding the source image and provides instructions to the image processor regarding how to modify the source image. These instructions may include, for example, image element by image element instructions or image frame by image frame instructions. For example, the instructions may direct image 1 to be given a first type of modification, image 2 to be given a second type of modification, image 3 to be given a third type of modification, etc. Each type of modification may be a global modification for the image or provide for multiple different modifications for different elements in the image.

The present invention also relates to stereo viewing glasses for converting a source image into a synthesized stereoscopic image. In one embodiment, the stereo viewing glasses include a first and second lens for receiving the source image, and an optic associated with at least one of the first and second lenses which modifies the spacial appearance of the source image such that the pair of lenses provide a pair of images having a different spacial appearance which, when viewed in combination, form a synthesized stereoscopic image. The stereo viewing glasses can include only optics, the images being formed by a separate image display. Alternatively, the stereo viewing glasses can include one or more image displays. These stereo viewing glasses can also incorporate existing optical techniques which have been used to create stereo effects.

In conjunction with forming synthesized stereoscopic images, the various embodiments of the present invention can be employed in a variety of applications where it is desirable to create a three dimensional depiction. For example, the present invention can be used to transform images formed in existing computer programs into stereoscopic images. Accordingly, the present invention can be used to enhance the appearance of cascaded windows being stacked over each other. Different windows can also be made to appear closer or farther from the observer.

The various embodiments of the present invention can also be employed in combinations with known pan and scan techniques to enhance the effectiveness of three dimensional imaging. For example, motion and depth can be introduced into a still picture by panning across the still picture. Meanwhile, depth can be introduced by modifying the panned image according the present invention. In combination, the modified, panned stereoscopic image has a significantly greater three dimensional appearance.

Another application of the present invention is in the area of medical tomography such as MRI and CT scans where a series of images are taken at different known depths. By distorting each image according to its known depth, the series of two dimensional images can be converted into a series of three dimensional images which more accurately reflect the tomography of the imaged body location. In addition to creating a three dimensional image based on an overlay of a set of two dimensional images, a sense of depth can be exaggerated in each two dimensional image, thus making it easier to distinguish elements in each image.

The present invention can also be used in medical endoscopy where two dimensional images taken from an endoscope are converted into three dimensional images by distorting the two dimensional image provided by the endoscope. By providing a stereoscopic endoscopic image as opposed to a two dimensional endoscopic image, the doctor is better able to determine the relative position of different objects in the field of view of the endoscope.

The present invention can also be used in combination with quicktime virtual reality applications where three dimension imaging is introduced into or enhanced in such applications.

BRIEF DESCRIPTION OF THE DRAWINGS

FIG. 1A illustrates a reduced right image.

FIG. 1B illustrates a magnified right image.

FIG. 1C illustrates a rotated right image.

FIG. 1D illustrates a right image which is skewed along the X axis as a function of the Y axis.

FIG. 1E illustrates a right image which is parabolically skewed along the X axis as a function of the Y axis.

FIG. 1F illustrates a right image which has a spherical distortion in causing the center of the image to appear at a different position in the Z axis relative to the X-Y plane.

FIG. 1G illustrates a portion of the right image being magnified.

FIG. 1H illustrates a center portion of the right image being magnified.

FIG. 1I illustrates a portion of the left image being magnified and a center portion of the right image being reduced.

FIGS. 6A–6G represent particular embodiments of the system illustrated with regard to FIG. 5.

FIG. 7A illustrates a set of tomographic images.

FIG. 7B illustrates a set of stereo pairs of the tomographic images illustrated in FIG. 7A.

FIG. 7C illustrates a set of stereo pairs of the tomographic images illustrated in FIG. 7A where particular images in the set of tomographic images are modified relative to each other to provide an improved stereoscopic description of those particular images in the set.

DETAILED DESCRIPTION OF PREFERRED EMBODIMENTS

Figure 1A:
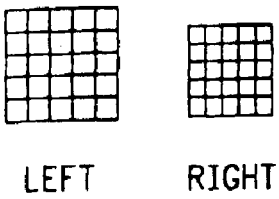
FIGS. 1A–I illustrate a series stereo pairs where at least the right image has been modified in a different manner than the left image.

The present invention relates to the discovery that the mind perceives two or more spatially different versions of the same image presented to the left and right eye as a synthesized stereoscopic image, i.e., as a three dimensional image. The present invention exploits this realization through methods, logic, data signals, recorded data, devices and stereoscopic imaging systems which convert a source image into a synthesized stereoscopic image by forming two or more images from the source image and modifying at least one of those images relative to the source image such that at least two of the images do not have the same spacial appearance as each other with or without regard to their distance.

In previous stereoscopic systems, synthesized stereoscopic images have been created using image shifting in combination with time delay, i.e., by controlling the time at which a same image is provided to the left and right eye of a viewer. An example of a time delay stereoscopic system is described in U.S. Pat. No. 5,510,832 which is incorporated herein by reference. By contrast to time delay based stereoscopic systems, the present invention creates synthesized stereoscopic images by forming two or more images which have a different spacial appearance. The use of images with a different spacial appearance according to the present invention can be done in combination with time delay or independent of time delay or motion.

Stereoscopic images have also been formed previously with the use of computers which calculate how the left and right eyes of a viewer would perceive each element of an image given the relative position of the left and right eyes to each element. The amount of computation required by this approach significantly limits its practicality for real time conversion of source images to stereoscopic images. In addition, it is necessary to know in advance the true depth of each element in the image at a given time in order to do the computation. By contrast, stereoscopic images are formed according to the present invention by modifying the source image without regard to simulating how each element of the source image would appear to the left and right eyes of the user if those elements were actually being seen by the user. Instead, elements of the source object or the entire source object are modified by an algorithm which causes the element or entire image to appear at a certain distance in the resultant stereoscopic image. By avoiding the need to precisely calculate how each element of the source object would appear to the left and right eyes of the user, the computational demands involved in the present invention are significantly reduced as compared to computer generated stereoscopic images. The reduced computational demands involved in the present invention enable stereoscopic images to be generated according to the present invention in real time. In instances where the relative depth of elements in an image are known, the present invention can modify these images to simulate the known depth without having to precisely calculate how each pixel of the image should appear in order to simulate depth.

Two or more images with different spacial appearances can be formed by magnifying, reducing, stretching (X axis or Y axis) rotating (X-Y plane) and/or tilting (rotating in X-Z and/or Y-Z planes) one or more of the images. A different spacial appearance can also be formed by modifying the relative position of elements in all or a portion of one or more of the images.

In one embodiment, modified stereo images are formed by taking a source image, forming two or more images from the source image, and transforming at least one of the two or more images using a function (f(x,y)) which alters the position along the X and/or Y axis of all or some of the objects appearing in the source image. The function may also serve to alter the image on a line by line basis when different functions can be used in different lines. Examples of transforming functions include distorting algorithms such as elliptical and aspheric algorithms, enlargements or offsets. In a preferred embodiment, the function is a non-linear distortion along the X and/or Y axes.

Any combination of the above modifications may be made on all or any portion of the right and/or left eye image in all or only some of the fields. More than one modification can also be made to the same image. In the case of stereoscopic imaging involving multiple frames (e.g., video), all or some of the multiple frames may have modified stereo pairs.

In embodiments where the present invention is used to generate three dimensional stereo graphics of a computer image, the modified stereo images may be formed by taking a source image and mapping the source image onto a wire mesh and distorting the image according to a function, such as those described herein and illustrated with regard to FIGS. 1A–I.

FIGS. 1A–I illustrate a series of modified stereo image pairs where at least the right eye image has been modified relative to the source image, illustrated as a uniform horizontally and vertically oriented grid. Although pairs of images are illustrated, it should be noted that sets of three or more images can also be formed.

Figure 1B:
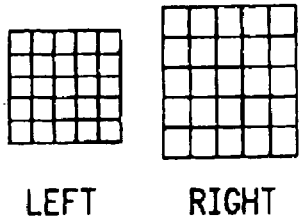
Figure 1C:
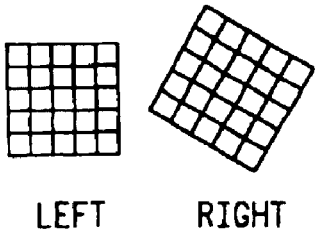
Figure 1D:
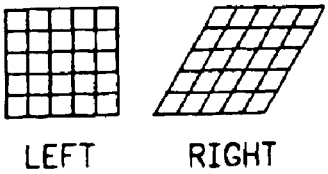
Figure 1E:
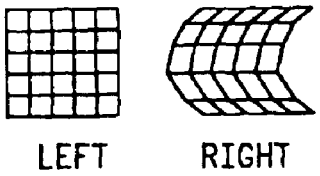
Figure 1F:
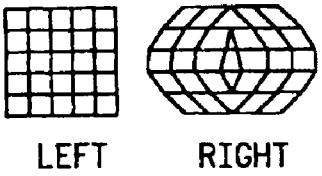
Figure 1G:
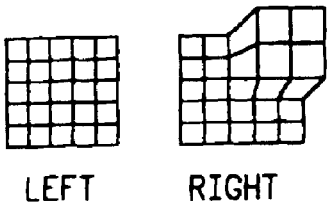
Figure 1H:
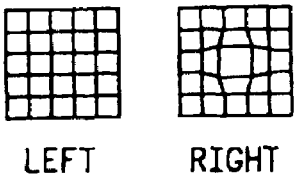
Figure 1I:
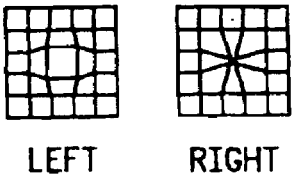

FIG. 1A illustrates a reduced right eye image. FIG. 1B illustrates a magnified right eye image. FIG. 1C illustrates a rotated right eye image. FIG. 1D illustrates a right eye image which is skewed along the X axis as a function of the Y axis. FIG. 1E illustrates a right eye image which is parabolically skewed along the X axis as a function of the Y axis. FIG. 1F illustrates a right eye image which has a spherical distortion in causing the center of the image to appear at a different position in the Z axis relative to the X-Y plane. FIG. 1G illustrates a right eye image where a portion of the image has been magnified. FIG. 1H illustrates a right eye image where the center of the image has been magnified. FIG. 1I Illustrates a left eye image with a magnified center portion and a right eye image with a reduced center portion. FIGS. 1A–I are intended to be illustrative of the various modifications which can be made to the source image in order to form modified stereo image pairs and are not intended to be exhaustive. These and other modifications to a source image to produce modified stereo image pairs can be created by a variety of digital or optical devices in real or non-real time without departing from the scope of the present invention.

In one particular embodiment, a pair of modified images are tilted or rotated in the X and/or Y and/or Z plane 10 percent or less relative to the other image. In another particular embodiment, a pair of modified images are magnified or reduced 10 percent or less relative to each other. In yet another particular embodiment, one of a pair of modified images is delayed one field or less relative to the other eye image. In all of the above embodiments, a convincing depth synthesis of these modified stereo image pairs occurs.

One example of a preferred transformation is the simultaneous warps of FIGS. 1B, 1F and 1H with 1 field or frame delay, horizontal offset of 3% and multiple target tracking with motion detection determining the direction of delay (i.e., on field 1 or 2), a 3% magnification of one image with the image mapped on a sphere twice the diameter of the screen with its axis displaced 2/3 up the height of the screen and with these effects oscillating from right to left eye image at 10 Hz.

Careful adjustment of all parameters of the video signal (or photographic, printed or film or computer image) as well as minimizing of parallax is necessary for good depth, minimal ghosting and comfortable viewing.

With ordinary stereo imaging, it is necessary to present the right eye image only to the right eye and the left eye image only to the left eye. If this is not done, confusing pseudoscopic images which cause eyestrain result. A unique feature of the present invention is that it is possible in some cases to present either image to either eye without pseudoscopy. This is made possible by the fact that the differences in the two or more images are created by modifying one or more of the images relative to a source image as opposed to relying on the relative spatial positions of the images at the time of photography or videography in order to cause the sensation of depth. Consequently, though FIG. 3A for example shows all the transforms being performed on one side, channel or element, in fact both sides, channels or elements may perform the same or different transforms to different degrees and such transforms or degrees may change over time in order to obtain maximum effect with minimum discomfort for the viewer.

Figure 2:
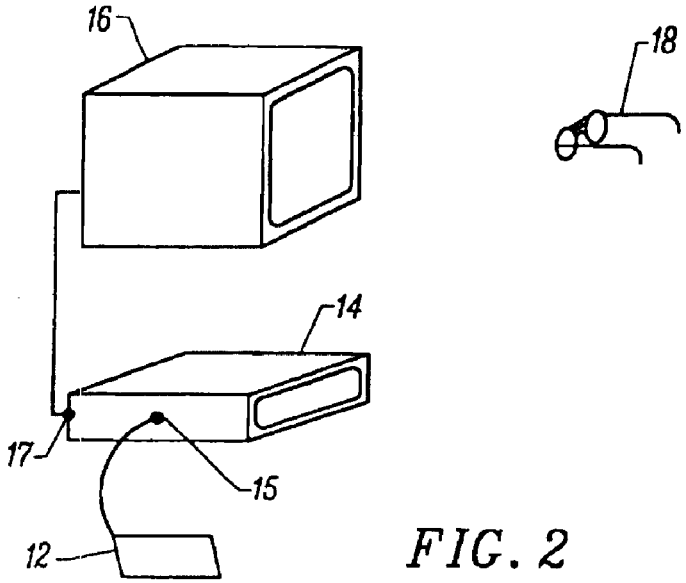
FIG. 2 illustrates a typical stereoscopic display system.

A typical stereoscopic display system is illustrated in FIG. 2. The system includes an image source 12, an image processor 14, an image display 16, and stereo viewing glasses 18. According to the present invention, the stereoscopic display system produces modified stereo images by taking a source image and forming a two or more images where at least one image has been modified relative to the source image and relative to the other images of the modified stereo images.

The formation of modified stereo images can be performed by several different components of a stereoscopic display system. For example, the image source 12 can provide image data corresponding to modified stereo images. Alternatively, the image processor 14 can receive image data from the image source 12 and convert the image data into modified stereo images according to the present invention. In this variation, the image data can also include instructions regarding how to modify the source image, for example, element by element or image by image. Alternatively, optics may be positioned between the image display and the user which convert images formed by the image display 16 into modified stereo images. For example, the lenses of stereo viewing glasses 18 may each receive the same image from the image display 16 and convert the image into modified stereo images according to the present invention. The stereo viewing glasses may optionally include the image display 16.

It is intended for the present invention to encompass image sources which provide image data encoding for modified stereo images according to the present invention as well as instrumentation for producing image data encoding for modified stereo images. The present invention also encompasses image processors which convert data for source images into image signals for modified stereo images according to the present invention. The present invention also encompasses optics which may be used to optically convert images produced by an image display into modified stereo images according to the present invention.

The present invention is also intended to encompass stereoscopic imaging systems which include an image source, image processor and/or optics which produce modified stereo images according to the present invention. In this regard, components of the system which are not being used to modify a source image to produce modified stereo image pairs may be standard equipment which is currently used in existing stereoscopic imaging systems.

The present invention is also intended to encompass methods employed by the above components of a stereoscopic imaging system for producing modified stereo images according to the present invention.

A significant advantage of the methods, devices and stereoscopic imaging systems of the present invention is their ability to convert existing two dimensional and three dimensional motion picture films, photos, computer images, videos and single cameras with ordinary lenses into a variety of stereo formats in real time or nonreal time. In the case of real time conversions, the methods and devices of the present invention may be used to convert unrecorded image signals, for example from a live broadcasts, video signals received via antenna or cable, or images from a computer program into a stereoscopic rendering of the program in full color and in real time.

A further advantage of the present invention is the ability to convert the source images into a series of different stereoscopic images based on the way in which the stereo images are modified relative to each other. Hence, the methods, devices and systems of the present invention are designed to be programmable to provide a series of different visual effects. In addition to the general solidizing or roundness of objects, one can make objects protrude from the screen and when combined with target acquisition and tracking performed on the same machine simultaneously with the other image manipulations described here, this stereosynthesis can be very sophisticated, real time and automatic. An object may be made to appear to recede into the background as it moves or becomes smaller. Further, artificial movement of an image, i.e. movement that occurs in the modified images but not in the source image, can be created by selecting a series of modification which introduce the sense of motion. Some elements in an image can be made to appear closer while other elements appear farther away. One can also detect foreground objects based on size or speed of motion and then magnify, delay, spherically warp or otherwise manipulate them selectively in real time automatically or for best effects, nonrealtime with more sophisticated algorithms or with human intervention using known means such as digitizing tablets and the like. It is also possible by these automatic means or with user intervention to select people or other objects by combining image acquisition with speech detection to create various types of games or contests from ordinary or specially encoded broadcast or prerecorded video.

A further advantage of the present invention is the limited computation that is required to convert the source images to stereoscopic images. Stereoscopic images have previously been formed by calculating how the left and right eyes of a viewer would perceive each element of an image given the relative position of the left and right eyes to each element. The amount of computation required by this approach significantly limits its practicality for real time conversion of the source images to stereoscopic images. By contrast, stereoscopic images are formed according to the present invention without regard to simulating how each element of the source image would appear to the left and right eyes of the user if those elements were actually being seen by the user. As a result, the computational demands involved in the present invention are significantly reduced as compared to computer generated stereoscopic images and thus can be generated in real time.

A further advantage of the present invention is the ability of the methods, devices and systems to convert the source images into three dimensional images in a single step. In this regard, aside from the component or components which are being used to form the pair of modified stereo images, the methods and devices of the present invention may be used with standard equipment. For example, except where modified stereo images are converted by the image viewer, full color stereoscopic images are viewable with inexpensive dual filter glasses (amaglyph glasses), LCD shutter glasses or other devices known in the art for controlled image transmission to the left and right eyes of the observer. Also, ordinary analog or digital video and/or computer hardware and/or software can be used.

A further advantage of the present invention is the color quality of the stereoscopic images produced. Because the conversion of source images to three dimensional images according to the present invention does not involve modifying the color of the source images, high quality full color stereoscopic images can be produced.

1. Image Source

In general, the image source 12 may be any recorded media, an image signal transmitter or data set which provides image data to the image processor 14. Examples of sources of recorded source images which can be readily converted into three dimensional images by the present invention include two dimensional and three dimensional motion picture films, photographs, computer images, and videos. In one particular example, the images are images generated by computer software. These image sources may be in a digital or analog format or in a real image format. Examples of recorded formats include, but are not limited to, videotape, magnetic media such as floppy discs, digital recorded media such as digital memory, digital tape, compact discs, DVD and the like. Examples of image transmitters include broadcast antenna, cable, fiber and satellite.

According to the present invention, the image source may be a standard image source which provides image data encoding standard two dimensional source images which are later processed by a component of a system according to the present invention to form modified stereo image pairs.

When the image source is an unmodified image as opposed to a modified stereo image, the image source may include a signal which provides instructions to an image processor regarding how to convert the signal encoding the source image into signals encoding the modified stereo images. These instructions may include, for example, image element by image element instructions or image frame by image frame instructions.

Alternatively, the image source may include image data creating modified stereo images. In this embodiment, the image source provides image data to the image processor corresponding to modified stereo images. The image processor receives the image data for the modified stereo images. This embodiment is a non-real time embodiment of the invention in the sense that the conversion of source images to modified stereo images is not being performed in real time by the system.

This embodiment of the invention enables standard video recording media (video tape, laser disc, DVD) to be used to store data encoding the stereoscopic images used in the present invention. By storing the data as opposed to converting source images to modified stereo images in real time, the processing speed requirements of the stereoscopic imaging system is greatly reduced.

Figure 3A:
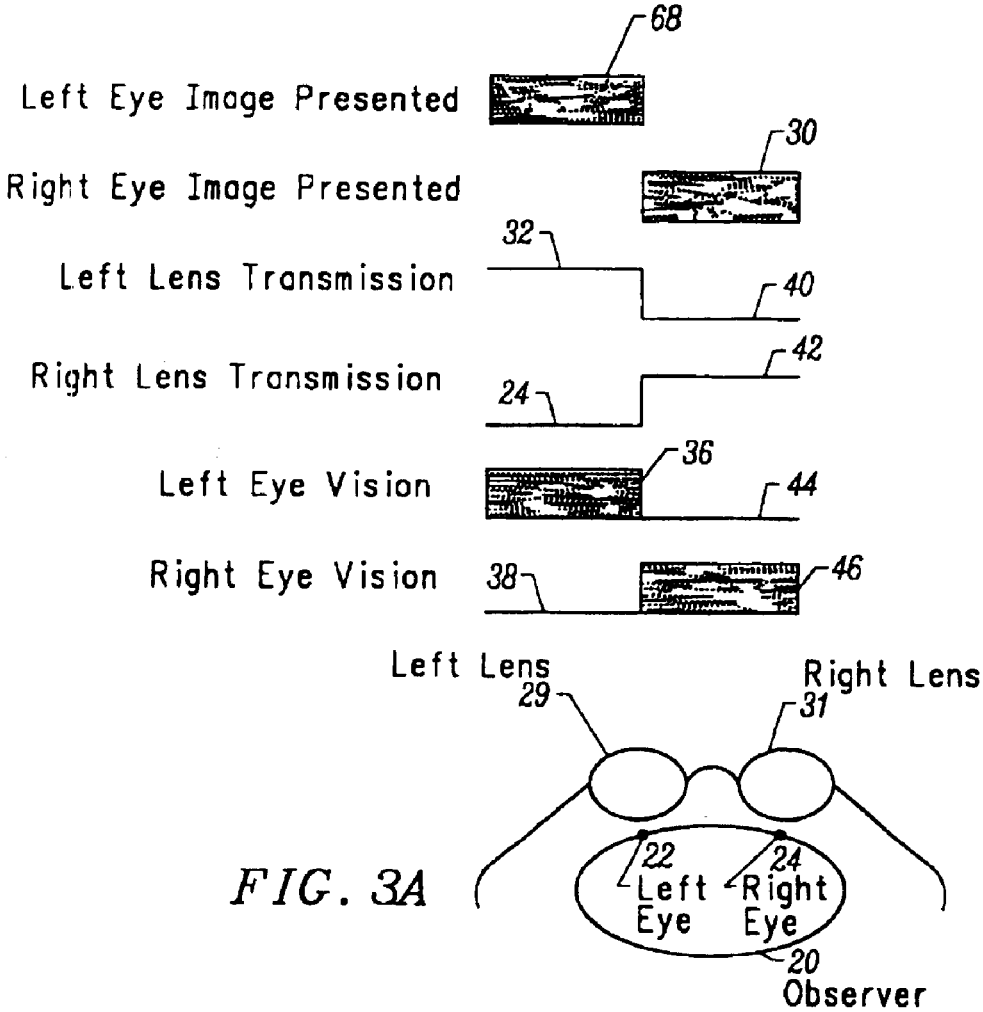
FIG. 3A is a timing diagram showing the transmission of left and right images to the eyes of a user of a time sequential stereoscopic system.
Figure 3B:
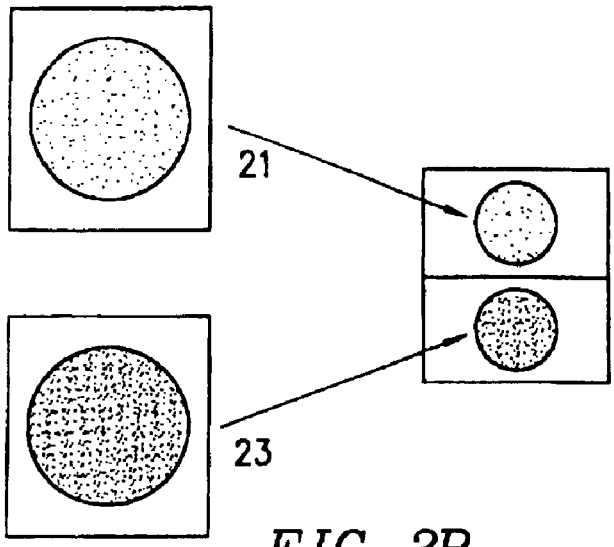
FIG. 3B illustrates an over-under format for displaying modified stereo images.

In embodiments where the image source provides image data encoding modified stereo images, the image data is preferably provided in an over/under or left/right format where two of the modified stereo images are placed on the same frame. In this format, a first image 21 from a set of modified stereo images is taken and condensed into an upper portion (or left portion) of an image frame. Meanwhile, a second image 23 from the set of modified stereo images is condensed into a lower portion (or right portion) of the same image frame, as illustrated in FIG. 3B. The first and second images 21, 23, although each being placed in only a portion of the image frame, are preferably non-interlaced images containing all the image data for the image. By contrast, the use of interlaced field images causes half the amount of image information to be stored per image frame.

Figure 3C:
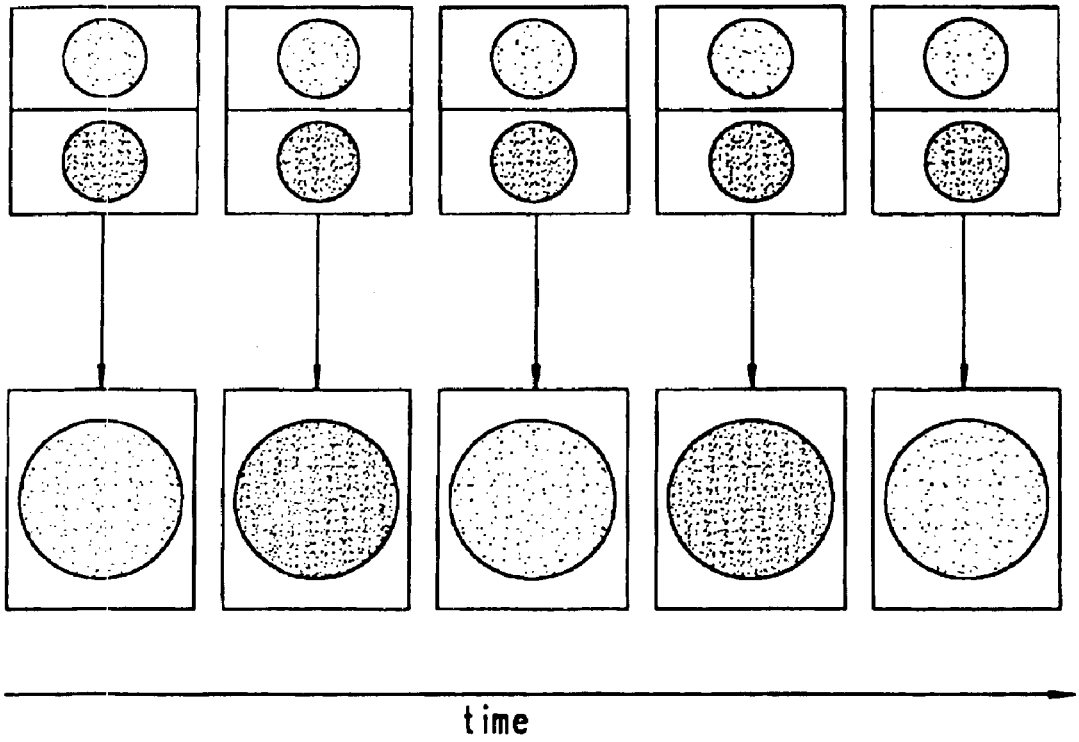
FIG. 3C illustrates a time sequence of a series of over-under image frames as in FIG. 3B where either a first or second image is displayed in each image frame.

FIG. 3C illustrates a time sequence of a series of over-under image frames as in FIG. 3B where either a first or second image 21, 23 is displayed in each image frame. Either the first or second image or the over-under image can be displayed from each image frame at a given time. Accordingly, you can have any combination of first (1) and second (2) images displayed in time sequence, (e.g., 12121212 or 11221122 or 111222 or 112112 or 111112, etc.). This approach provides the system of the present invention with significantly greater flexibility for producing visual effects based on displaying different combinations of first and second images. For example, this approach can be used to create certain visual effects, such as the movement of an image element laterally across the screen. By controlling whether an image element is shown to the left or right eye, the appearance of movement by the image element laterally across the image can be created or enhanced.

The use of an over/under or left/right format has further advantage of enabling different visual effects to be performed. For example, line averaging between two left or two right eye frames can be performed.

In one embodiment, computer software is used as described in "UNIVERSAL STEREOSCOPIC INTERFACE," U.S. Provisional Application Ser. No.: 60/013,738; filed: Mar. 20, 1996; and "UNIVERSAL STEREOSCOPIC INTERFACE," U.S. application Ser. No.: 08/280,570; filed: Mar. 19, 1997, each of which are incorporated herein by reference. This computer software enables one to distinguish between and selectively display different images of a pair of images presented in an over/under format. This software is useful for increasing the range of display formats which can be used with the modified stereo image pairs used in the present invention.

2. Image Processor and Image Display

In general, the image processor 14 receives image data via a signal entry port 15. The image processor 14 includes logic for converting the image data into image signals encoding the source image and for modifying at least one of the image signals such that the image signals encode images having a different spacial appearance. The image processor also includes a signal exit port 17 for transmitting the modified first and second image signals to an image display 16 which displays real images corresponding to the modified image signals. Examples of image displays include, but are not limited to, screens associated with projection systems, televisions, CRT screens, VR or holography.

Standard image displays such as television sets have a refresh rate of 15.25 KHz which is above the frequency at which the human eye can perceive individual images. As a result, the image displays appear to present a continuous image. Presenting alternating left and right eye images effectively causes an image display to have an effective refresh rate that is half the normal refresh rate of that display. If the refresh rate falls below the frequency at which the human eye can perceive images, the mind perceives the display as flickering which can cause eye strain and headaches. In order to eliminate this effect, it is preferred to increase the rate at which lines or entire images are presented. This can be done by line doubling, frequency doubling or frame multiplication techniques which can be performed before or after the source image is modified.

In the embodiment described in Section 1, the image processor receives image data from an image source corresponding to modified stereo image. Alternatively, the image processor can receive image data from an image source corresponding to a source image and produce an image signal for the source image.

In a particular embodiment of the invention, the image processor converts image data from an image source encoding a standard source image into image signals encoding modified stereo images. In this embodiment, the image processor takes image data from the image source and forms signals for images where at least one of the images has been modified relative to the source image such that the modified images do not have the same spacial appearance. Processing of the image data from the image source into modified stereo images may be done in real time or not in real time by the image processor and recorded. The signals inputted into the image processor and outputted by the image processor may be analog or digital signals.

In a preferred embodiment, the image processor includes logic for performing multiple different transformations of a source image to produce different modified stereo images based on a source image. The different modified stereo images are produced by different transformations of the source image to create different visual effects. For example, certain transformations increase or decrease the depth of field or field of view provided.

The different transformation performed by the image processor may be selectable by the observer, thereby providing the observer with control over the visual effects produced. For example, the user can select transformations which cause certain elements of an image to appear closer or farther away relative to their appearance in a source image. The user can also select among different transformations which introduce different degrees of spatially transformations to increase or decrease the disparity perceived between close and distant elements in the same image. In this regard, the observer can design the appearance of the resulting stereoscopic images. The ability of an observer to customize the stereoscopic imagery produced is an important feature of the present invention since how stereoscopic images are perceived varies from person to person.

The image processor can include logic which controls how the image processor transforms the source image based on the source image. This logic can correspond to software or a computer chip encoding the logic. The logic can be used to enable the image processor to dynamically adjust itself to optimize the stereoscopic appearance of different images or elements in images. For example, the logic can be used to detect motion in the source image and modify the source image to make the images appear closer or farther away based on the motion detected. The logic can also be used for special effects to create the appearance of motion of elements of the image which are stationary in the source image.

The logic of the image processor can also be used as an editing tool to make certain objects appear closer or farther away. The ability to magnify or reduce the appearance of elements within an image is an important application of the present invention in conjunction with film editing, such as pan and scan. This type of editing tool is also useful in conjunction allowing an observer to customize the appearance of a stereoscopic image, for example by allowing an observer to select which images or elements of an image to magnify, reduce or distort. Another application of this editing tool is in the computer software arena where an observer selects which elements of a stationary computer generated image the observer wishes to bring into the foreground or the background.

For optimal depth with minimal eyestrain, it is desirable to carefully adjust the effects on each shot of a program and to have them vary timewise. It is also desirable to design the image processor to permit the user to control which image transformation is performed. For instance, the entire right eye frame or parts of a frame may be delayed one field, magnified 5 percent and horizontally shifted 7 percent while the right half of the image is tilted back in the Z axis 6 percent, an object in the middle convexly projected on a spherical surface of diameter 3 times the screen height, while the left eye image may be untransformed or have an object in its center magnified 8 percent, the left half given vertical rugose transforms, the top half concavely projected on a dodecahedron with smallest 4 times the screen width etc. These transforms could change in kind and vary in degree and from one eye's field to the other either slowly or as rapidly as every field with all these parameters preprogrammed or under user control.

Conversion of image data encoding a source image to an image signal encoding modified stereo images can be performed formed in real time by analog and/or digital devices or by computer software. Conversion could also be done with a single video stream from digital or analog source or from dual streams. In cases where field delay or field advancement is desired, this could be introduced by running two copies of the same tape, disc or digital source one or more fields out of sync or by picking fields as desired from an analog or digital store in real or nonreal time. Common examples of such sources and stores are betacam SP or D1 tapes, nonlinear edit systems, frame store, computer hard drives and RAM, CDROM, laserdisc and DVD.

With advanced hardware and/or software and especially with non-real time systems, with human operator input or with automatic image segmentation and pattern recognition techniques known in the art, parts of the source image can be designated for particular transforms and followed from frame to frame by the program. For instance, a human figure can be identified, given a five percent convex transform and one field delay in the left eye until it disappeared from the scene or the scene changed. Parts of the image can be transformed in this manner and composited and recomposited into the image.

Delays or advancement of one or more field or parts of fields can be part of the synthesized difference between the images presented to the two eyes. Ideally, the delay will be one field or less and will depend on the direction and speed of motion. With most sequences of moving images, such delay introduces spurious vertical parallax and pseudoscopic imagery which looks odd and creates eyestrain. Non-real time shot to shot editing is essential for use of delay and is desirable for all the other image transforms as well. For many sequences, no delay will give the best results. Delay can be applied to only part of the field instead of or in addition to the whole field.

3. Stereo Viewing Glasses

The stereo viewing glasses 18 operate in combination with the image display 16 to coordinate what images are provided to the left and right eyes 22, 24 of the observer 20. By controlling which images are provided to the left and right eyes and/or the timing of when those images are provided, an impression of a three dimensional image can be created from a pair of two dimensional images. For example, FIG. 3A illustrates an image display 16 for use with flicker glasses to control what images are observed by the left and right eyes of the observer. As illustrated, when a left image 28 is presented, the left lens 29 of the stereo viewing glasses 18 transmits the left image while the right lens 31 blocks or absorbs the left image 28. This allows the left eye of the observer to see the left image 28, while the right eye does not see the left image 28. When the right image 30 is presented, the lens transmissions are reversed so that the right eye sees the right image and the left eye does not see the left image. By alternating between the left and right image, the observer's brain receives both images and synthesizes the two images into a single image which the brain interprets as having depth.

The stereo viewing glasses 18 may have optical, electrooptic or mechanical lenses. In one preferred embodiment, each lens is activated electronically to block the light reaching the eyes alternately. The glasses may be gelatin, glass, dichroic polarized, anaglyphic, or holographic filters or optical or electrooptic and need only have appropriate optical characteristics.

Although the invention is described primarily with regard to filter or shutter glasses, any other display modality may be used such as displaying right and left stereo pairs in frame, field, line or pixel sequential form or as simultaneous pairs for stereoscopic or autostereoscopic viewing. In one embodiment of the present invention, the images are presented autostereoscopically by known means without the use of stereo viewing glasses. For example, the stereo viewing glasses can have polarized lens. Then, by controlling the polarization of the light, different images can be directed to the left and right eyes. Alternatively, the stereo viewing glasses can have red/green and blue filters on the left and right eyes respectively. Then, by transmitting one image in red and green light and the other image in blue light, different images can be selectively transmitted to the left and right eyes of the observer. Other mechanisms for presenting different images to the left and right eyes of the observer that are known in the art or later developed and are intended to be used in the present invention.

Figure 4:
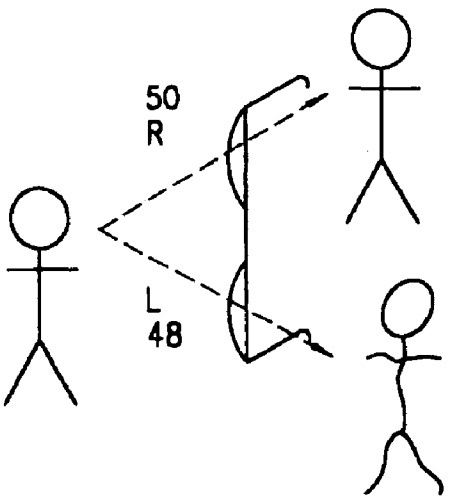
FIG. 4 shows the effect of optical lenses used in one embodiment of the invention.

In another embodiment of the invention, modified image pairs may be formed by optics positioned between the image display and the observer which selectively modify left or right eye images produced by the image display. For example, the image display or the stereo viewing glasses may include optics which modify a source object produced by the image display such that modified pairs of left and right eye images are produced. FIG. 4 shows the effect of one type of lens used in accordance with the present invention. In this embodiment, the left eye lens 48 does not transform the image produced by the image display. Meanwhile, the right eye lens 50 modifies the right eye image according to the present invention. The brain combines the left and right images to produce a single image which is perceived as having depth. In this simplest case, there is no electronic processing of the two dimensional image and the glasses are composed of optical elements which distort or transform the image differently for each eye such that the viewer obtains a sensation of depth.

4. Systems for Forming Synthesized Stereoscopic Images

Figure 5:
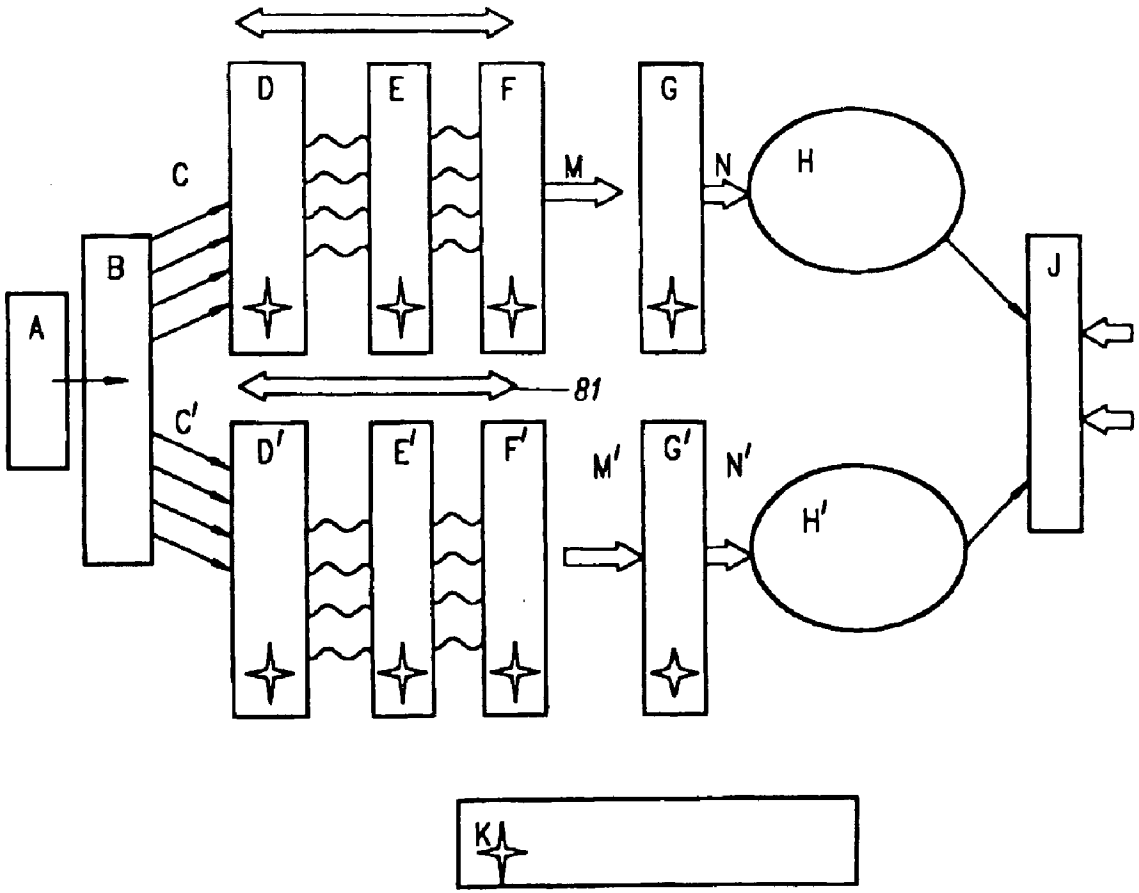
FIG. 5 illustrates a generalization of a system for producing synthesized stereoscopic images.

The following example describes different systems for forming synthesized stereoscopic images. FIG. 5 illustrates a generalization of the overall system. FIGS. 6A–6G represent particular embodiments of the system illustrated with regard to FIG. 5.

As illustrated in FIG. 5, A represents a two dimensional data set of a source image. The data set can be an analog or digital data set. The data set is copied by device B which can be an optical image duplicator or signal distribution amplifier. Signals C and C' represent at least two copies of the data set encoding the source image which are conveyed to separate sets of image processors, represented as processors D, E and F and D', E' and F'. A greater or lesser number of image processors can be used than are illustrated. The data sets encoding the source image are spatially altered by the processors according to one or more functions for modifying the image, such as the functions that have been described herein. The signals from the processors can be resent through the different processors as many times as desired, as illustrated by long arrows 81.

Device K controls the qualities of the spatial distortions introduced into the image signals M, M' by the processors, further modifications of the image signals M, M' by devices G and G', and/or the signals N, N' that are sent to image display devices H, H'. Devices G and G' may perform a variety of functions including, for example, frequency doubling or other modifications which provide image enhancement. Device J represents the different techniques for combining two or more images to produce stereoscopic images including, for example, sequential and optical field multiplexing, such as shutter glasses or polarized lenses. Device J can also represent a device for recording the image signals as digital or analog data sets.

Figure 6A:
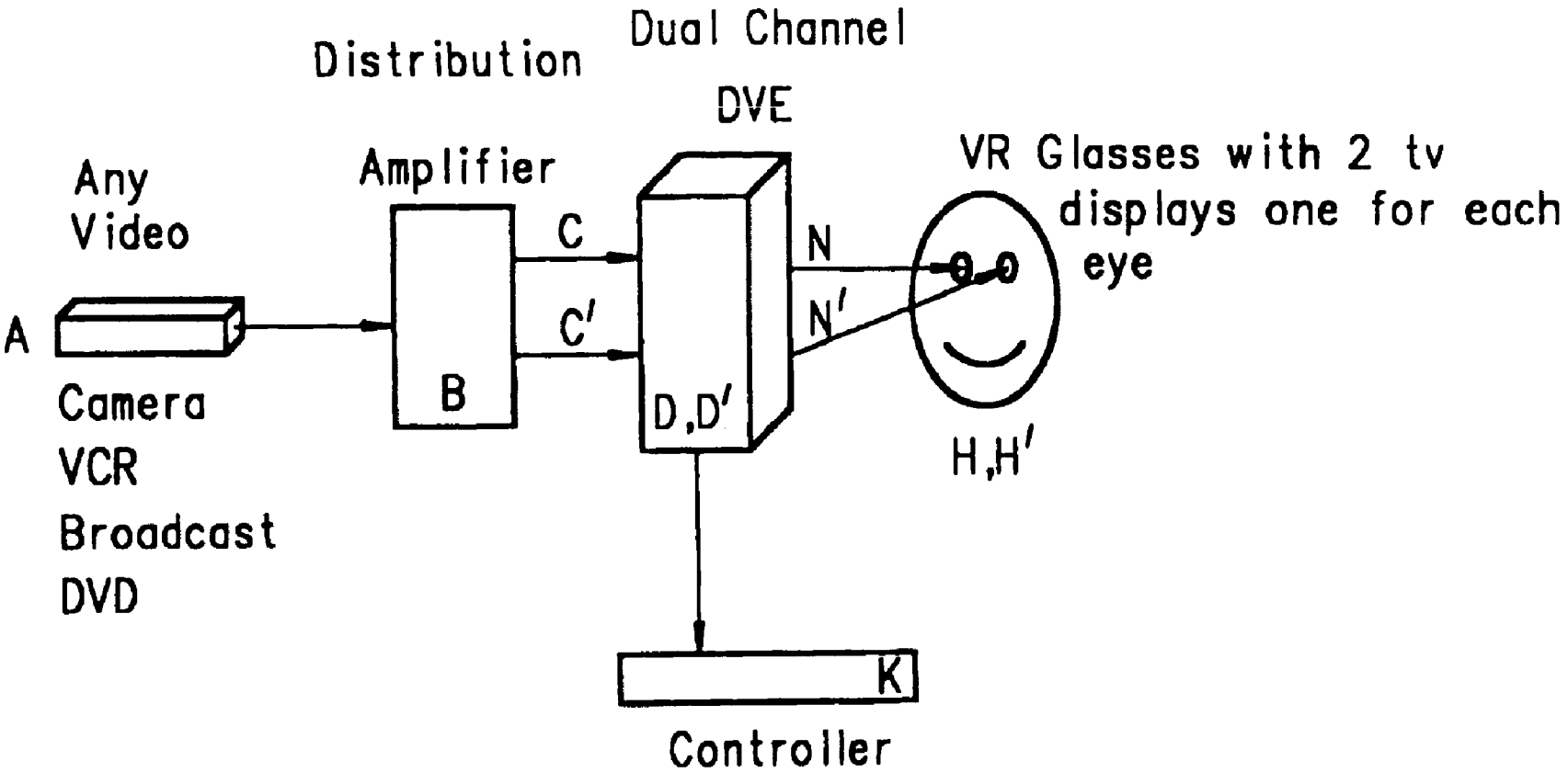

FIG. 6A illustrates an embodiment of the system illustrated in FIG. 5 where A represents any video signal source including for example, a camera, VCR, broadcast signal or DVD. Device B represents a signal distribution amplifier. Image processing in this system is performed by a dual channel video effects device (DVE) D, D' which is controlled by controller K. In this embodiment, image display devices H, H' are virtually reality (VR) glasses with dual video displays, one for each eye.

Figure 6B:
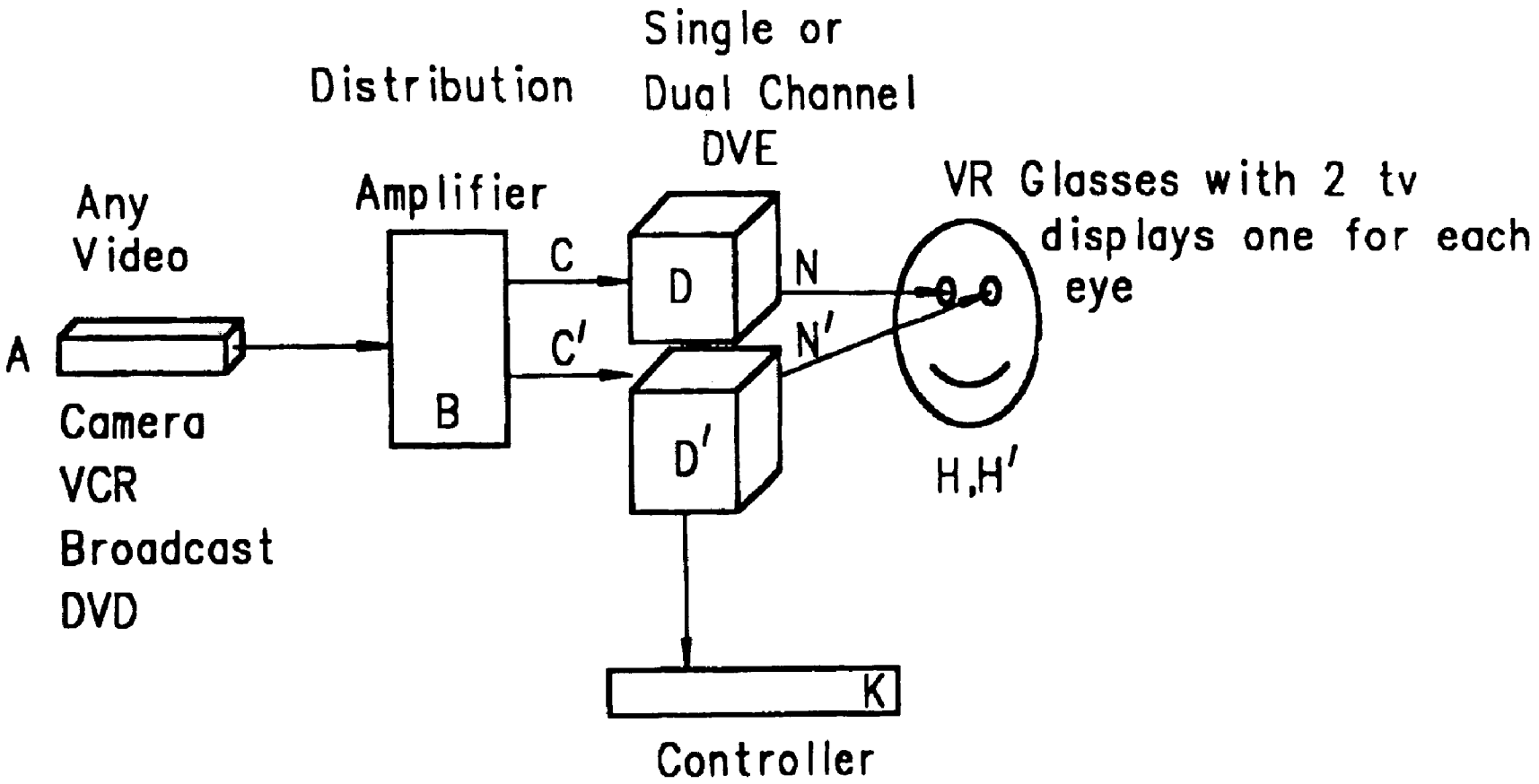

FIG. 6B illustrates an alternate embodiment of the system illustrated in FIG. 5 where A represents any video signal source and device B represents a signal distribution amplifier. Image processing in this system is performed by a single DVE D which is controlled by controller K. An optional second DVE D' is also illustrated which can optionally alter image signal N' relative to the source image. In this embodiment, image display devices H, H' are virtual reality (VR) glasses with dual video displays, one for each eye.

Figure 6C:
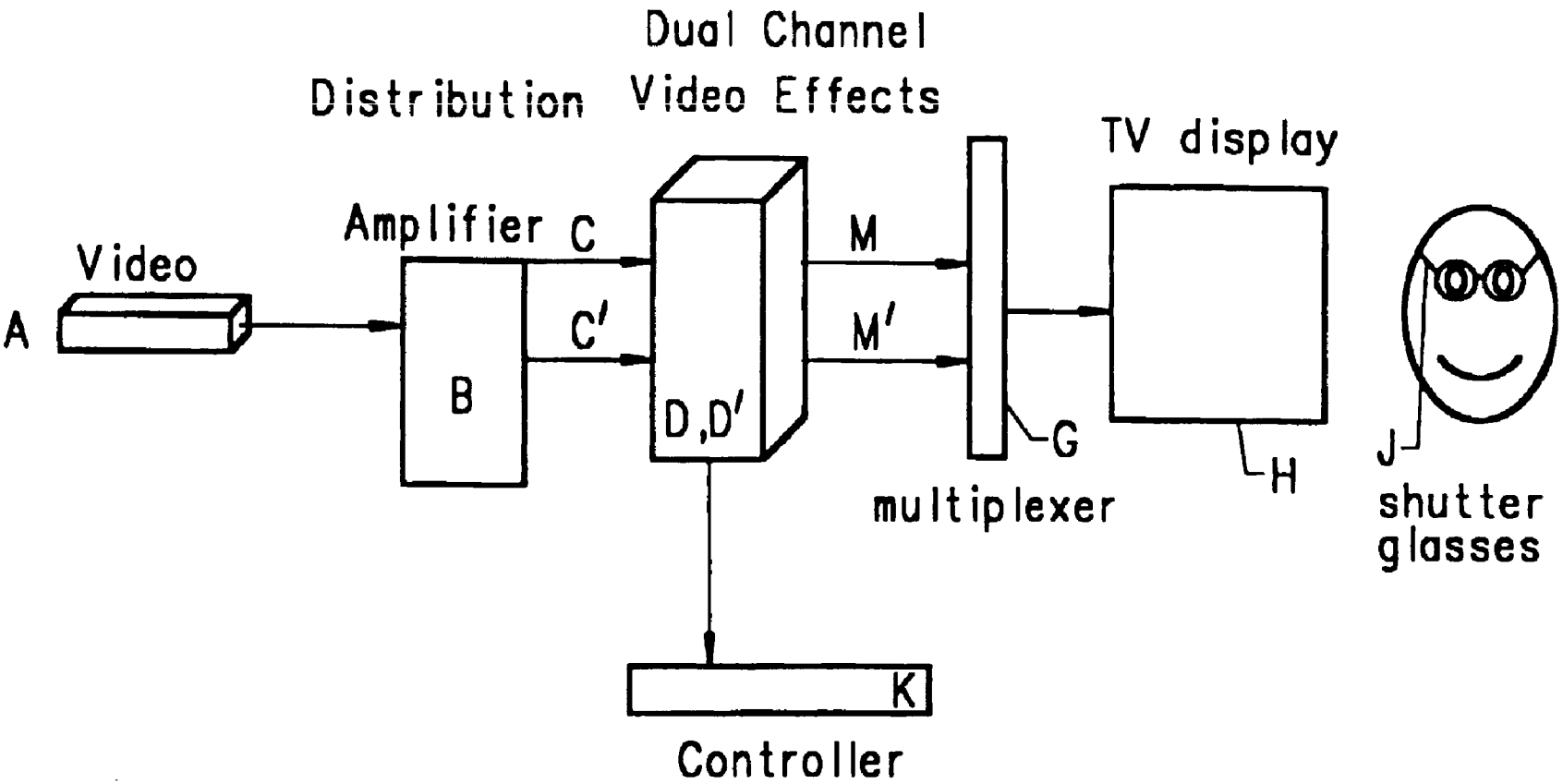

FIG. 6C illustrates another alternate embodiment of the system illustrated in FIG. 5 where A represents any video signal source and device B represents a signal distribution amplifier. Image processing in this system is performed by DVE D, D' which is controlled by controller K. In this embodiment, a multiplexer G field sequentially multiplex signals M and M'. The multiplexed image signals M and M' are displayed on video display H (e.g., a TV or computer monitor). Shutter glasses J combine the multiplexed images displayed on video display H. J can alternatively be polarized lenses where the video display H displays multiplexed images formed of light with different polarizations.

Figure 6D:
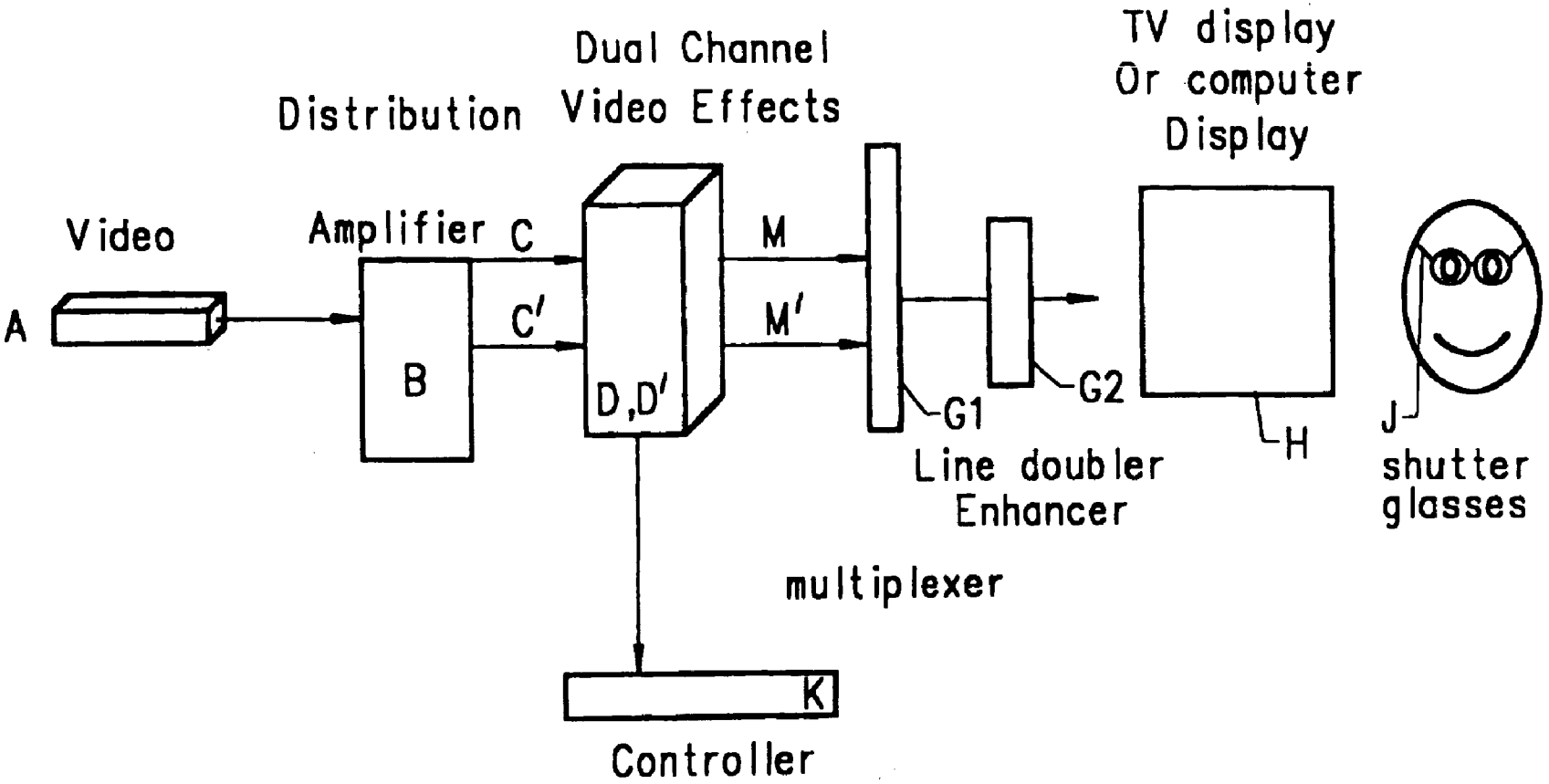

FIG. 6D illustrates another alternate embodiment of the system illustrated in FIG. 5 where A represents any video signal source, device B represents a signal distribution amplifier, D, D' represent an DVE image processor and K represents a controller. In this embodiment, a multiplexer G1 field sequentially multiplexes signals M and M' while line doubler G2 increases the refresh rate at which images are displayed on video display H. Line doubler G2 can also include the functionality of a picture enhancer for providing edge improvement. Shutter glasses J combine the multiplexed images displayed on video display H.

Figure 6E:
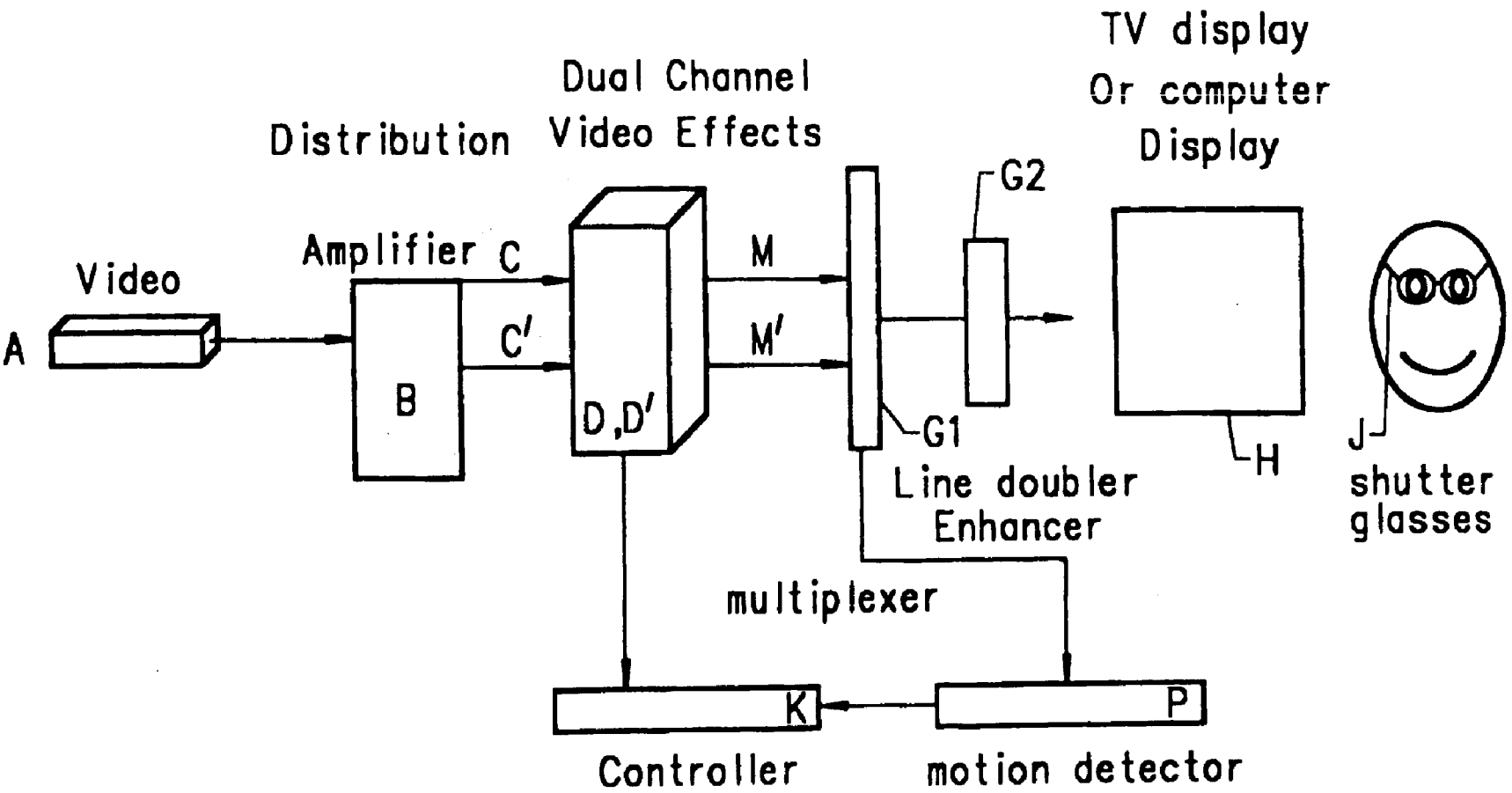

FIG. 6E illustrates a variation of FIG. 6D where the system further includes a motion detector P which detects motion of elements of an image, e.g., whether a camera is panning from right to left, left to right, up, down, etc. Device P can alternately be used to detect whether a particular image element is close or distant in order to determine what transformation to use. Based on the type of motion detected by motion detector P, the controller K determines which image (encoded by M and M') to display first. When the multiplexer G1 is used to combine the images encoded by M and M' in an over-under format, motion detector P can also by used to determine which image (encoded by M and M') the display H should display first.

The motion detector P can also be used to detect motion in an image, the detection of which is used by the controller K to direct the processor D, D' to modify the image signals to show that an element of an image is moving in a particular direction. For example, the detection of an element moving toward the screen can be used by the controller to direct the processor to modify the images to make the element appear closer in the stereoscopic image, thereby enhancing the stereoscopic effect.

Figure 6F:
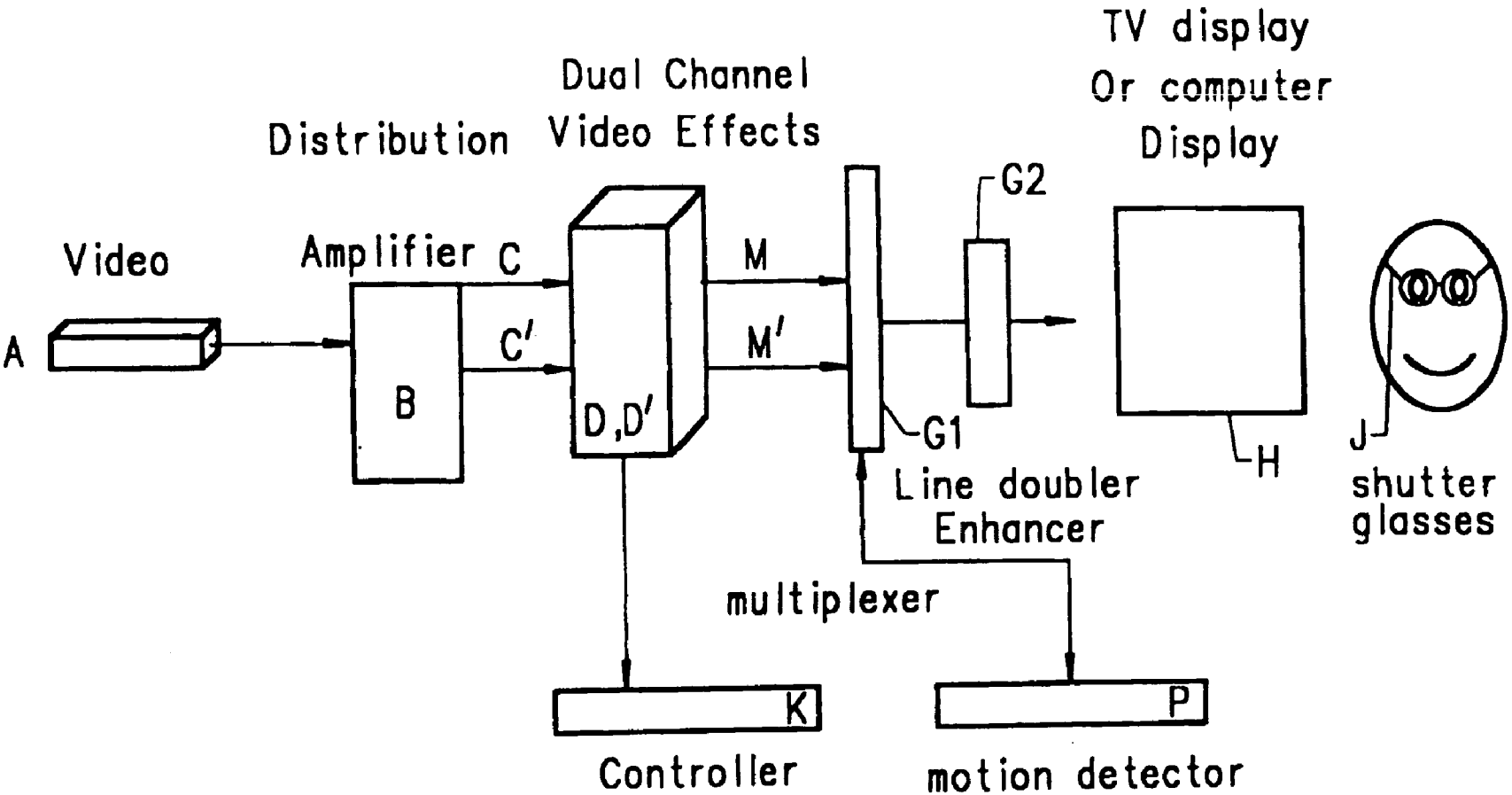

FIG. 6F illustrates an alternate variation of FIG. 6D where the system further includes a motion detector P which is only connected to the multiplexer. In this embodiment, the motion detector P is used to detect motion of elements in an image, e.g., whether a camera is panning from right to left, left to right, up, down, etc, and uses this information to determine which image (encoded by M and M') the image display H should display first. When the multiplexer G1 is used to combine the images encoded by M and M' in an over-under format, motion detector P can also be used to determine which image (encoded by M and M') the display H should display first.

6. Stereographic Imaging of Sets of Tomographic Images

The following example illustrates the modification of a set of tomographic images to provide improved stereographic imaging of the set of tomographic images. In this example, a set of tomographic images, illustrated in FIG. 7A is taken and converted into stereo pairs of the tomographic images, illustrated in FIG. 7B, where the pair of images formed of each slice has a different spacial appearance relative to each other. As illustrated in FIG. 7C, only particular images of the set of tomographic images are modified relative to each other to provide an improved stereoscopic depiction of those particular images in the set.

7. Tomographic Imaging Application

Figure 8A:
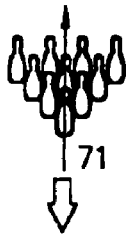
FIG. 8A illustrates a set of bowling pins.
Figures 8B, 8C, 8D, 8E:
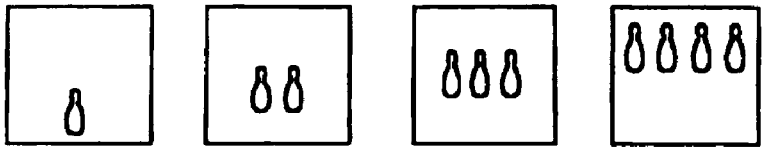
FIGS. 8B–8E illustrate a series of two-dimensional tomographic images of the set of bowling pins where each image shows a different row of pins.
Figures 8F, 8G:
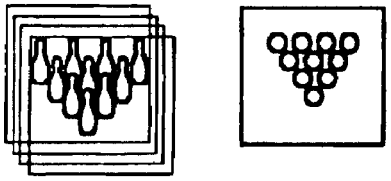
FIG. 8F illustrates a stereoscopic image of the bowling pins created from the tomographic images illustrated in FIGS. 8B–8E.
FIG. 8G illustrates a top down view of the image illustrated in FIG. 8F.

The following example describes a tomography application for the devices and methods of the present invention for generating a synthesized stereoscopic image from a two dimensional source image. FIG. 8A illustrates a three dimensional object, in this case a set of bowling pins viewed along axis 71. FIGS. 8B–8E illustrate a series of two-dimensional tomographic images of the set of bowling pins taken along axis 71 where each image shows a different row of pins, intended to represent a different depth layer of the three dimensional image. By taking the four tomographic images illustrated in FIGS. 8B–8E, distorting each image in relation to its relative position within the three dimensional image, and overlaying the four images, a stereoscopic image of the bowling pins can be created, as illustrated in FIG. 8F. A data matrix can then be formed of the different elements (bowling pins) as they appear in the overlaid stereoscopic image. FIG. 8G illustrates a top down view of the data matrix illustrated in FIG. 8F.

Figure 8H:
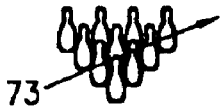
FIG. 8H illustrates the set of bowling pins illustrated in FIG. 8A and a second viewing axis.
Figures 8I, 8J, 8K, 8L:
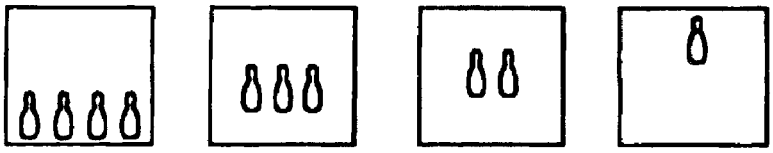
FIGS. 8I–8L illustrates a series of two-dimensional tomographic images of the set of bowling pins taken along the second viewing axis.

Using the data matrix illustrated in FIGS. 8F and 8G, it is possible to generate different sets of two dimensional images taken along different viewing axes. For example, FIG. 8H illustrates the set of bowling pins illustrated in FIG. 8A and a viewing axis 73. FIGS. 8I–8L illustrates a series of two-dimensional tomographic images of the set of bowling pins taken along axis 73. Using the set of two dimensional images, it is then possible to distort each image as a function of its position along axis 73 and overlay the images to form a new stereoscopic image illustrating the appearance of the object along the viewing axis 73, as illustrated in FIG. 8M.

Figures 8M, 8N:
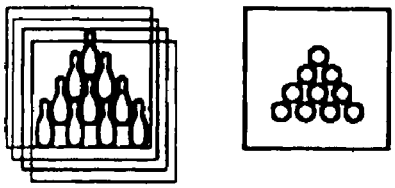
FIG. 8M illustrates a stereoscopic image of the bowling pins created from the tomographic images illustrated in FIGS. 8I–8L.
FIG. 8N illustrates a top down view of the image illustrated in FIG. 8M.

FIG. 8N illustrates a top down depiction of the stereoscopic image illustrated in FIG. 8M.

As illustrated by FIGS. 8A–8N, it is possible to convert a series of tomographic images of an object and use the methods and devices of the present invention to create different synthesized stereoscopic images of the object along different viewing axes. This application of the present invention is particularly useful in medical applications like MRI and CT imaging where it is desirable to be able to create different three dimensional renderings of an object in order to identify the relative positions of different elements of the object. For example, by viewing a three dimensional rendering of an object at different angles, it is possible to more accurately determine the relative positions of different elements within an object.

In one variation of this example, an observer attaches a mechanism to his or her head which can detect head motion. The head movement mechanism is coupled to the system for generating the stereoscopic images and is used to direct different stereoscopic images to be generated based on the angle or position of the observer's head, as determined by the head movement mechanism. This enables an observer, for example, to turn his or her head sideways or up or down in order to view the stereoscopic image of the object at different angles. The system, in a preferred embodiment, is able to track the head movement and modify the stereoscopic image accordingly in real time.

8. Stereographic Display of Computer Images

Figure 9:
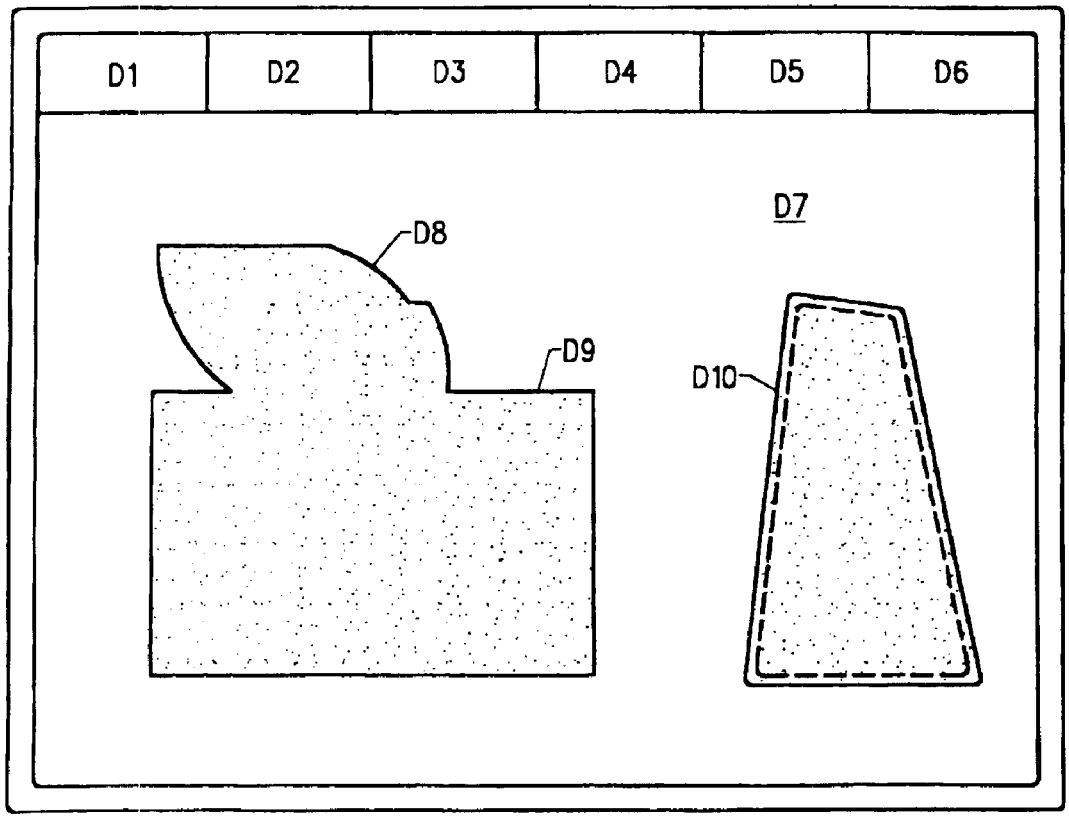
FIG. 9 illustrates different images on a computer monitor where each image has a user selectable three dimensional appearance.

The following example describes a method for forming stereographic display of a computer image. Illustrated in FIG. 9 are regions D1 through D10 which represent images displayed on a computer monitor according to the present invention which appear to have separate three dimensional appearances when viewed using shutter glasses, polarized plates or anaglyph techniques or other three dimensional imaging techniques.

According to this example, the software program receive data encoding a source image as input, forms modified stereo images of the source image, and then texture maps the image by applying a function to the source image, and then texture maps the image to modify the appearance of the entire source image based on that function, as opposed to forming a stereographic image by calculating how each pixel of each image would appear to the left and right eyes of the user.

The software program can be used to independently texture map the different images represented by D1 through D10 in order to create independent stereographic appearances for each image based on the particular modified stereo images formed, i.e., different modifications cause the images to have a different stereographic appearance. The software program can generate the stereographic appearance of these images automatically. Alternatively, the user can direct the software program to perform different modifications such that each image has a user selected stereographic appearance. Thus the software enables the user to create his or her own stereographic display of a series of images which can be modified as the user desires.

9. Stereographic Display of Computer Images

In embodiments where the present invention is used to generate three dimensional stereo graphics of a computer image, the modified stereo images may be formed by taking a source image and forming two more modified images according to the present invention. This may be done, for example, by mapping the source image onto two wire frame meshes and then distorting at least one of the images by the distorting one or both of the wire frame meshes onto which the source image is mapped. An equivalent effect to distorting the wire frame meshes can be done via mathematical manipulation of data encoding the source image.

Figure 10A:
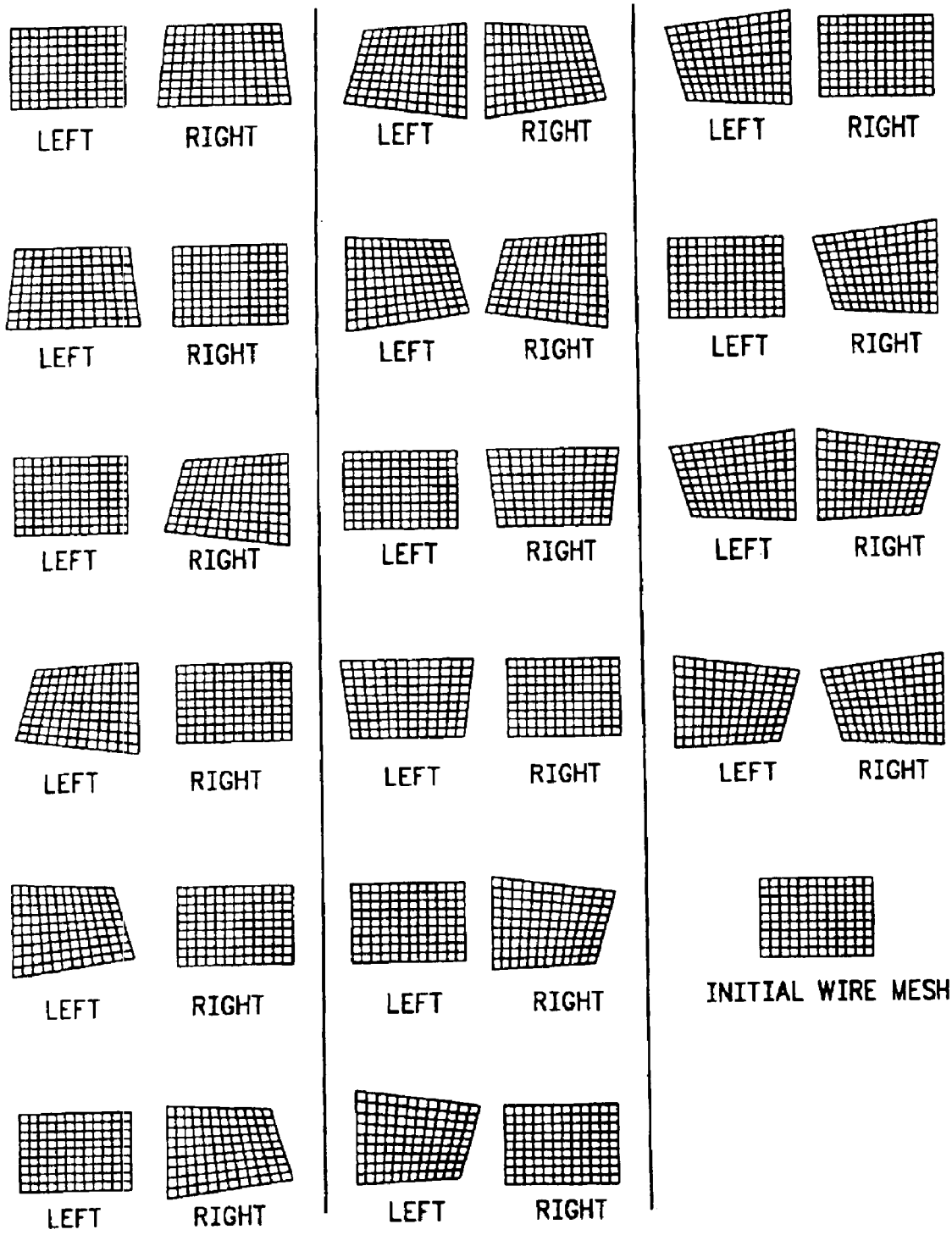
FIG. 10 illustrates examples of different pairs of wire meshes which can be generated by modifying the wire frame mesh illustrated in the figure as the initial wire mesh.
Figure 10B:
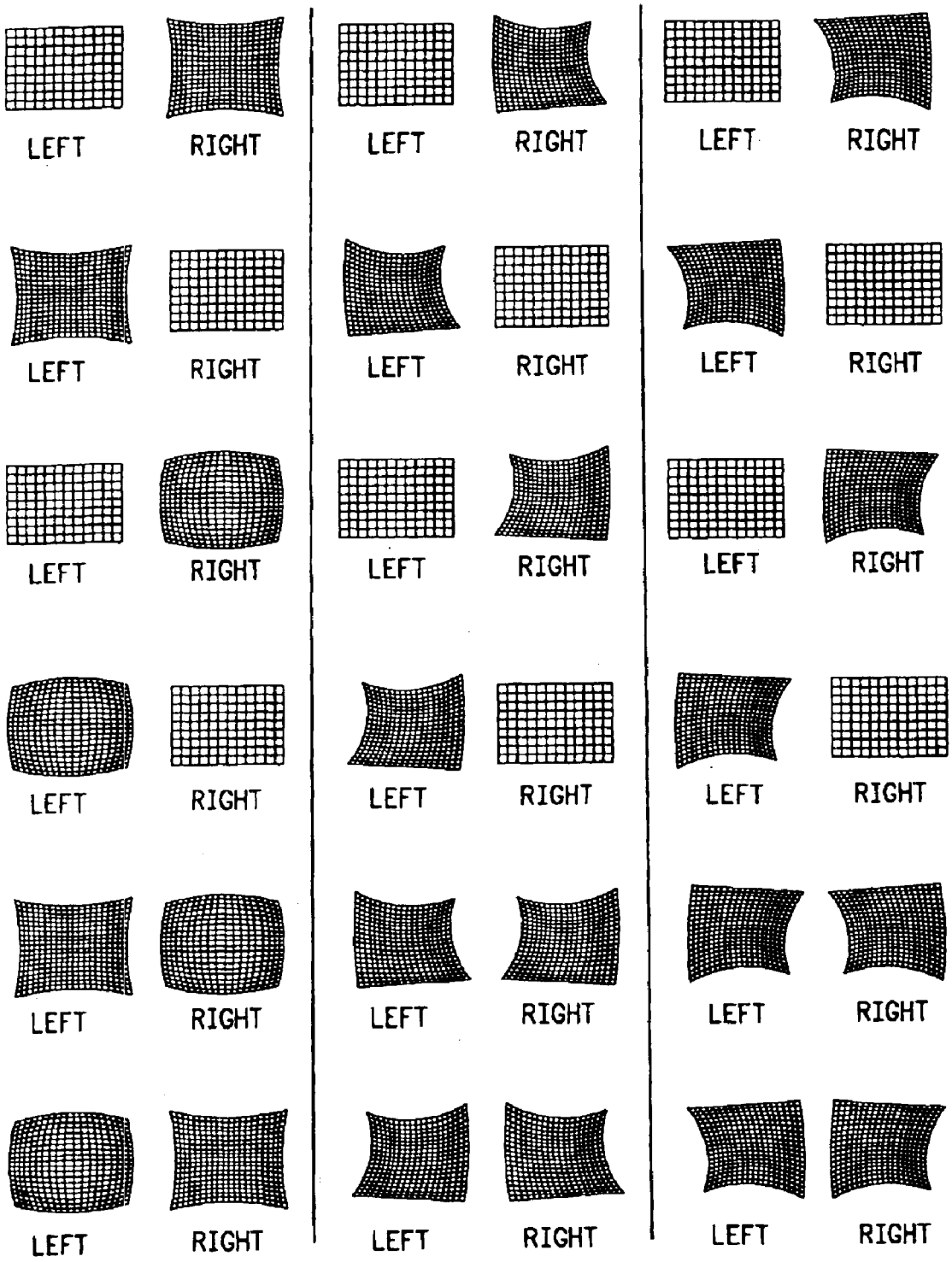
Figure 10C:
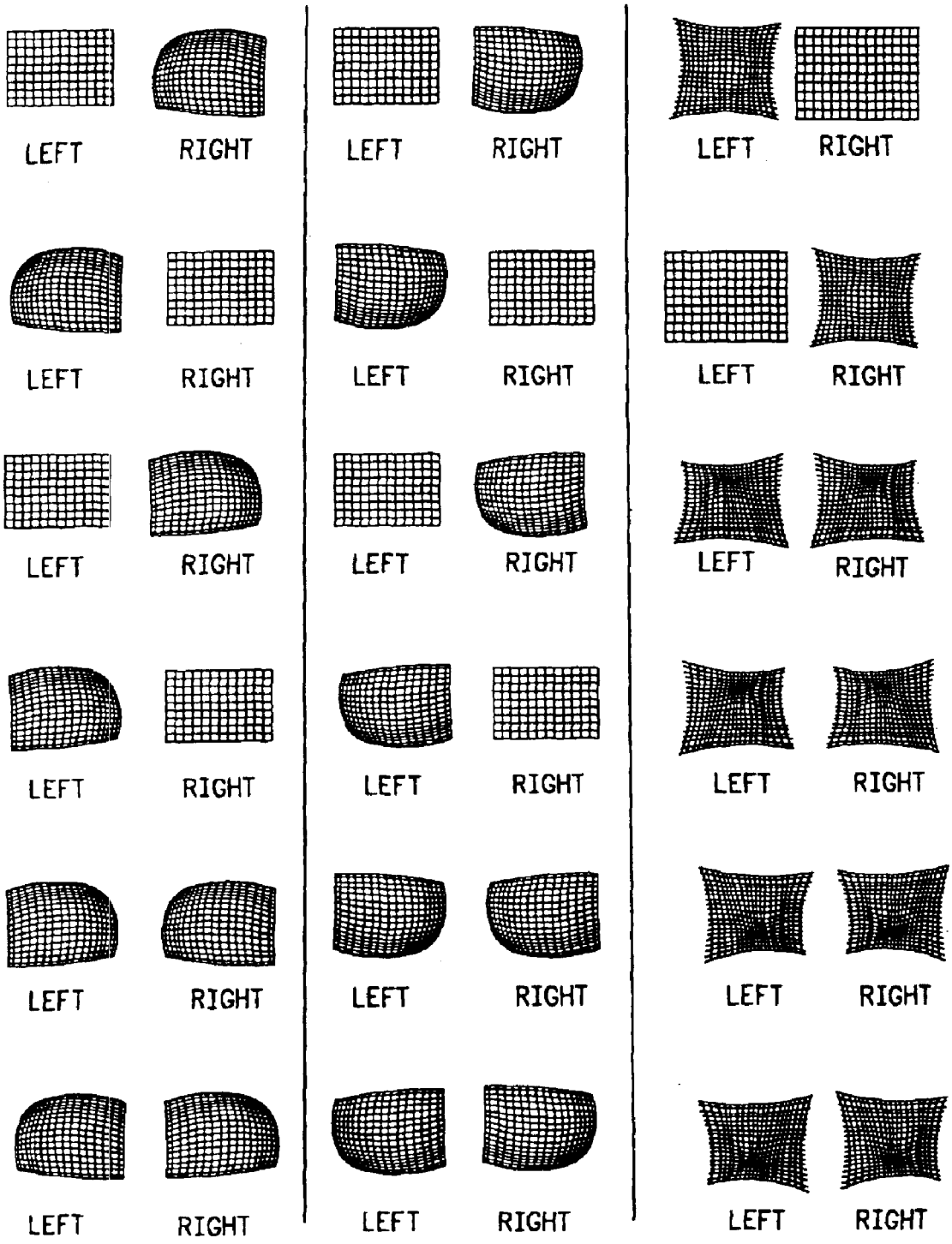

FIG. 10 illustrates examples of different pairs of wire meshes which can be generated by modifying the wire mesh illustrated in the figure as the initial wire mesh. By mapping a source image onto two initial wire meshes for the left and right eyes and then distorting one or both of the wire meshes as illustrated in the figure, a stereo pair of images can be created.

10. Image Data Management Protocol for Image Displays

In one embodiment, image data for a given line of an image is received and modified according to the present invention into data for a stereo pair of the given line. According to this protocol, each line of the stereo pair of lines is then displayed to the left and right eye respectively before new image data for same given line is received and displayed. This is accomplished by increasing the frequency at which a given line is presented to the left or right eye. As a result, the same number of lines are presented over time to each of the left and right eyes as would be presented to the left and right eyes if the line data were not modified according to the present invention. The above protocol may be used with interlaced or noninterlaced displays known as multiple frequency monitors.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for producing a synthesized stereoscopic image of a source image comprising:

displaying at least two images which when viewed in combination form the synthesized stereoscopic image of the source image, do not simulate how a physical three dimensional model of the source image would independently appear to a left eye and a right eye of an observer, and include one image which differs from another of the at least two images such that at least a portion of the one image is magnified, reduced, rotated, displaced in a vertical direction, or modified such that a position of one or more elements of that image relative to other elements of that image is different than relative positionings of the corresponding elements in another of the at least two images.

2. The method according to claim 1, wherein the step of displaying the at least two images includes transmitting the image signals encoding the at least two images to an image display.

3. The method according to claim 2 wherein at least one of the image signals is an analog signal.

4. The method according to claim 2 wherein at least one of the image signals is a digital signal.

5. The method according to claim 2, wherein the image signals are transmitted to the image display by a device which converts recorded data encoding the at least two images into the image signals.

6. The method according to claim 2, wherein the image signals are transmitted to the image display by a device which converts a signal encoding the source image into the image signals.

7. The method according to claim 6, wherein converting the signal encoding the source image into the image signals is performed by the device in real time.

8. The method according to claim 1, wherein only one image of the at least two images is modified relative to the source image.

9. The method according to claim 1, wherein at least two of the at least two images are modified relative to the source image.

10. The method according to claim 1, wherein one of the at least two images is magnified or reduced relative to another of the at least two images.

11. The method according to claim 1, wherein one of the at least two images is rotated in the X and/or Y and/or Z plane relative to another of the at least two images.

12. The method according to claim 1, wherein images for a given eye are displayed at a frequency that is greater than the frequency at which that eye can perceive individual images.

13. The method according to claim 1, wherein a position of one or more elements of one of the at least two images relative to other elements of that image is different than relative positionings of the corresponding elements in another of the at least two images.

14. The method according to claim 1, wherein at least one of the at least two images is transformed relative to the source image using a function which alters the position of elements of the image along the Y axis.

15. The method according to claim 1, wherein wherein at least one of the at least two images is transformed relative to the source image using a function which is a distorting algorithm.

16. The method according to claim 1, wherein at least one of the at least two images is transformed relative to the source image using a function which is an elliptical or aspheric algorithm.

17. The method according to claim 1, wherein at least one of the at least two images is transformed relative to the source image using a function which is nonlinear along at least one of the X and Y axes.

18. A method for viewing a synthesized stereoscopic image comprising:

displaying a source image on an image display; and viewing the source image through stereo viewing glasses, the stereo viewing glasses having left and right lenses, at least one of the lenses modifying the source image to produce at least two images which when viewed in combination form the synthesized stereoscopic image of the source image, do not simulate how a physical three dimensional model of the source image would independently appear to a left eye and a right eye of an observer, and include one image which differs from another of the at least two images such that at least a portion of the one image is magnified, reduced, rotated displaced in a vertical direction, or modified such that a position of one or more elements of that image relative to other elements of that image is different than relative positionings of the corresponding elements in another of the at least two images.

19. The method according to claim 18, wherein modifying the source image to produce the at least two images is performed in real time.

20. The method according to claim 18, wherein only one of the at least two images is modified relative to the source image.

21. The method according to claim 18, wherein at least two of the at least two images are modified relative to the source image.

22. The method according to claim 18, wherein one of the at least two images is magnified or reduced relative to another of the at least two images.

23. The method according to claim 18, wherein one of the at least two images is rotated in the X and/or Y and/or Z plane relative to another of the at least two images.

24. The method according to claim 18, wherein images for a given eye are displayed at a frequency that is greater than the frequency at which that eye can perceive individual images.

25. The method according to claim 18, wherein a position of one or more elements of one of the at least two images relative to other elements of that image is different than relative positionings of the corresponding elements in another of the at least two images.

26. The method according to claim 18, wherein at least one of the at least two images is transformed relative to the source image using a function which alters the position of elements of the image along the Y axis.

27. The method according to claim 18, wherein at least one of the at least two images is transformed relative to the source image using a function which is nonlinear along at least one of the X and Y axes.

28. A method for synthesizing stereoscopic image from a source image comprising:

taking a signal encoding a source image and forming at least two image signals encoding the source image;

modifying at least one of the image signals such that the image signals encode at least two images which when viewed in combination form the synthesized stereoscopic image of the source image, do not simulate how a physical three dimensional model of the source image would independently appear to a left eye and a right eye of an observer, and include one image which differs from another of the at least two images such that at least a portion of the one image is magnified, reduced, rotated, displaced in a vertical direction, or modified such that a position of one or more elements of that image relative to other elements of that image is different than relative positionings of the corresponding elements in another of the at least two images; and displaying on an image display the at least two images encoded by the modified image signals.

29. The method according to claim 28, wherein modifying at least one of the image signals is performed in real time.

30. The method according to claim 28 wherein the modification of the source image involves a signal conversion selected from the group consisting of digital to digital, digital to analog, analog to digital and analog to analog.

31. The method according to claim 28, wherein only one of the at least two images is modified relative to the source image.

32. The method according to claim 28, wherein at least two of the at least two images are modified relative to the source image.

33. The method according to claim 28, wherein one of the at least two images is magnified or reduced relative to another of the at least two images.

34. The method according to claim 28, wherein one of the at least two images is rotated in the X and/or Y and/or Z plane relative to another of the at least two images.

35. The method according to claim 28, wherein a position of one or more elements of one of the at least two images relative to other elements of that image is different than relative positionings of the corresponding elements in another of the at least two images.

36. The method according to claim 28, wherein at least one of the at least two images is transformed relative to the source image using a function which alters the position of elements of the transformed image along the Y axis.

37. The method according to claim 28, wherein at least one of the it least two images is transformed relative to the source image using a function which is nonlinear along at least one of the X and Y axes.

38. The method according to claim 28, wherein wherein at least one of the at least two images is transformed relative to the source image using a function which is a distorting algorithm.

39. The method according to claim 28, wherein at least one of the at least two images is transformed relative to the source image using a function which is an elliptical or aspheric algorithm.

40. The method according to claim 28 wherein at least one of the at least two images includes a horizontal or vertical shift relative to the source image.

*41. The method according to claim 1, wherein at least one of the at least two images is transformed relative to the source image using a function which alters the position of elements of the image along the X axis.*

*42. The method according to claim 1, wherein some or all of at least one of the at least two images is transformed relative to the source image based on speed of motion.*

*43. The method according to claim 1, further comprising the step of determining the position of each of the one or more elements of that image relative to other elements of that image based on variable delay.*

*44. The method according to claim 43, wherein determining the position of each of the one or more elements of the transformed image relative to other elements of that image based on variable delay comprises:*

*determining the position of any one of the one or more elements of the transformed image based on the speed of motion of that one element.*

*45. The method according to claim 43, wherein determining the position of each of the one or more elements of the transformed image relative to other elements of that image based on variable delay comprises:*

*determining the position of any one of the one or more elements of the transformed image based on a functions of the relative speed of one or more of the objects and or background of the image.*

*46. The method according to claim 1, wherein the position of the one or more elements of that image are determined based on encoding information.*

*47. The method according to claim 46, wherein the encoding information comprises information obtained while encoding the image signals.*

*48. The method according to claim 18, wherein at least one of the at least two images is transformed relative to the source image using a function which alters the position of elements of the image along the X axis.*

*49. The method according to claim 18, wherein some or all of at least one of the at least two images is transformed relative to the source image based on speed of motion.*

*50. The method according to claim 18, further comprising the step of determining the position of each of the one or more elements of that image relative to other elements of that image based on variable delay.*

*51. The method according to claim 50, wherein determining the position of each of the one or more elements of that image relative to other elements of that image based on variable delay comprises:*

*determining the position of any one of the one or more elements of that image based on the speed of motion of that one element.*

*52. The method according to claim 50, wherein determining the position of each of the one or more elements of the transformed image relative to other elements of that image based on variable delay comprises:*

*determining the position of any one of the one or more elements of the transformed image based on a functions of the relative speed of one or more of the objects and or background of the image.*

*53. The method according to claim 18, wherein the position of the one or more elements of that image are determined based on encoding information.*

*54. The method according to claim 53, wherein the encoding information comprises information obtained while encoding the image signals.*

*55. The method according to claim 28, wherein at least one of the at least two images is transformed relative to the source image using a function which alters the position of elements of the image along the X axis.*

*56. The method according to claim 28, wherein some or all of at least one of the at least two images is transformed relative to the source image based on speed of motion.*

*57. The method according to claim 28, further comprising the step of determining the position of each of the one or more elements of that image relative to other elements of that image based on variable delay.*

*58. The method according to claim 55, wherein determining the position of each of the one or more elements of that image relative to other elements of that image based on variable delay comprises:*

*determining the position of any one of the one or more elements of that image based on the speed of motion of that one element.*

*59. The method according to claim 57, wherein determining the position of each of the one or more elements of the transformed image relative to other elements of that image based on variable delay comprises:*

*determining the position of any one of the one or more elements of the transformed image based on a functions of the relative speed of one or more of the objects and or background of the image.*

*60. The method according to claim 28, wherein the position of the one or more elements of that image are determined based on encoding information.*

*61. The method according to claim 60, wherein the encoding information comprises information obtained while encoding the image signals.*

* * * * *